(12) United States Patent
Schonfeld et al.

(10) Patent No.: US 10,524,876 B2
(45) Date of Patent: Jan. 7, 2020

(54) SYSTEM FOR MONITORING CLEANING EFFORTS OF CAREGIVERS USING STETHOSCOPES

(71) Applicants: Alvin J. Schonfeld, Chicago, IL (US); Ryan A. Schonfeld, Hawthorne, CA (US)

(72) Inventors: Alvin J. Schonfeld, Chicago, IL (US); Ryan A. Schonfeld, Hawthorne, CA (US)

(73) Assignee: CLEAN SCOPE, LLC., Chicago, IL (US)

( * ) Notice: Subject to any disclaimer, the term of this patent is extended or adjusted under 35 U.S.C. 154(b) by 0 days.

(21) Appl. No.: 15/916,820

(22) Filed: Mar. 9, 2018

(65) Prior Publication Data

US 2018/0200022 A1 Jul. 19, 2018

Related U.S. Application Data

(63) Continuation-in-part of application No. 14/868,749, filed on Sep. 29, 2015, now Pat. No. 9,949,713.

(51) Int. Cl.
*A61B 90/70* (2016.01)
*A61L 2/28* (2006.01)
(Continued)

(52) U.S. Cl.
CPC .............. *A61B 90/70* (2016.02); *A61B 7/02* (2013.01); *A61B 90/90* (2016.02); *A61L 2/28* (2013.01);
(Continued)

(58) Field of Classification Search
CPC ...................................................... A61B 90/70
See application file for complete search history.

(56) References Cited

U.S. PATENT DOCUMENTS 6,018,835 A 2/2000 Schonfeld
7,406,973 B1 8/2008 Redman et al.
(Continued)

OTHER PUBLICATIONS

Gabriele Messina, et al.; A new UV-LED device for automatic disinfection of stethoscope membrane; undated; pp. 1 through 6; American Journal of Infection Control.
(Continued)

*Primary Examiner* — Jason Y Ko
(74) *Attorney, Agent, or Firm* — Law Office of John W. Harbst

(57) ABSTRACT

A system for monitoring cleaning efforts of care givers using stethoscopes including one or more stations capable of cleaning a head portion of a stethoscope presented thereto. The system includes an identification apparatus operably associated with each of a plurality of stethoscopes. The identification apparatus serves to identify a particular stethoscope and, thus, a particular care provider. A mechanism for detecting and signaling each time a particular stethoscope comes within predetermined radius of a cleaning station forms part of the system. Another mechanism for detecting and signaling each time a particular stethoscope is presented to a station to have a cleaning event performed thereon also forms part of the system. An analysis unit is operably connected to each detecting mechanism and is configured for calculating the cleanliness level of each stethoscope. A method for monitoring cleaning efforts of care providers using stethoscopes is also disclosed.

23 Claims, 11 Drawing Sheets

(51) Int. Cl.
*A61B 7/02* (2006.01)
*A61B 90/90* (2016.01)
(52) U.S. Cl.
CPC ....... *A61L 2202/14* (2013.01); *A61L 2202/17* (2013.01); *A61L 2202/24* (2013.01)

(56) References Cited

U.S. PATENT DOCUMENTS

| | | |
|---|---|---|
| 8,795,438 B2 | 8/2014 | Rubin et al. |
| 9,114,184 B2 | 8/2015 | Messina et al. |
| 2009/0224907 A1 | 9/2009 | Sinha et al. |
| 2011/0197921 A1* | 8/2011 | Rubin ................. A61L 2/28 134/18 |
| 2012/0051969 A1 | 3/2012 | Nahman et al. |
| 2013/0178718 A1 | 7/2013 | Tran |
| 2016/0089214 A1 | 3/2016 | Schonfeld et al. |

OTHER PUBLICATIONS

International Searching Authority, International Search Report in re International PCT Patent Application PCT/US2019/021588; dated Jun. 5, 2019.

Written Opinion of the International Searching Authority issued in connection with International PCT Patent Application PCT/US2019/021588, dated Jun. 5, 2019.

* cited by examiner

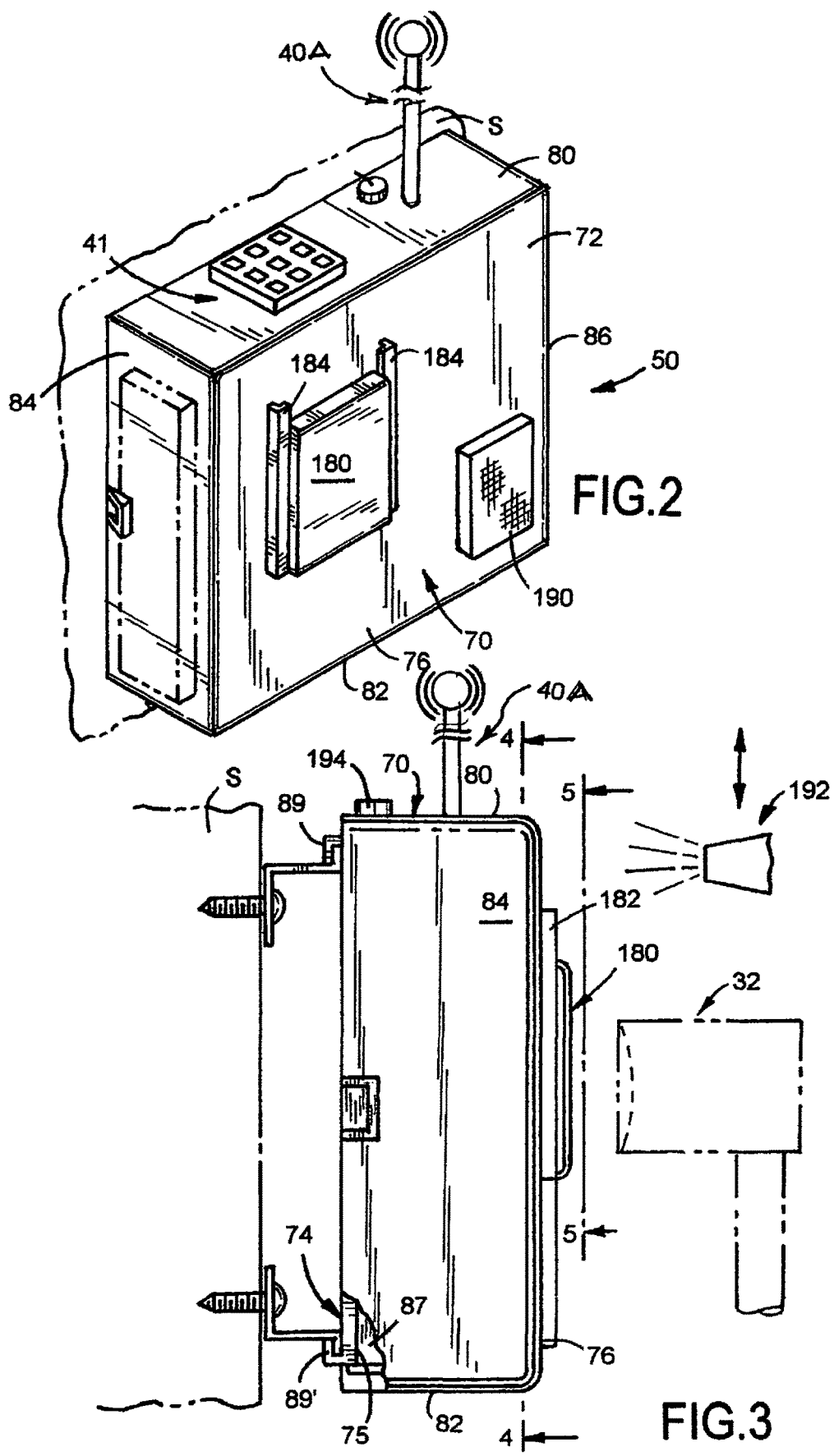

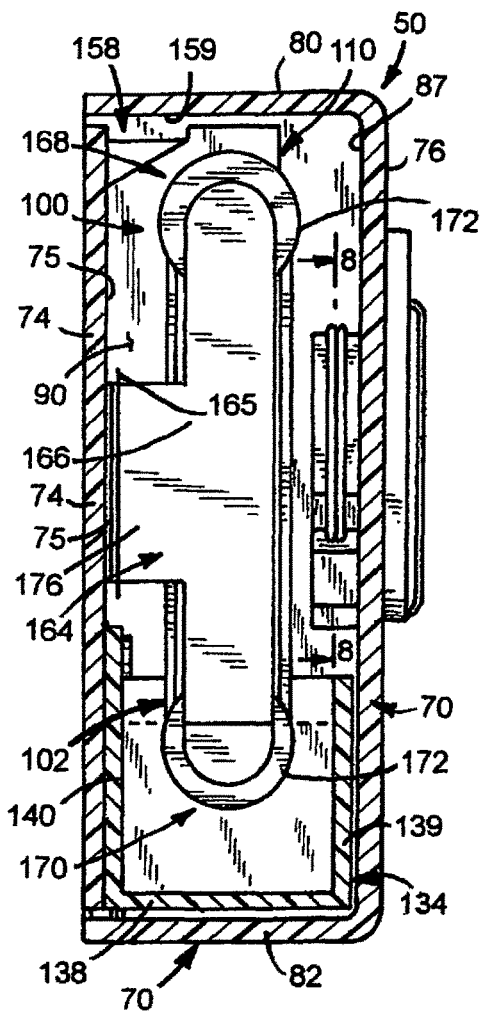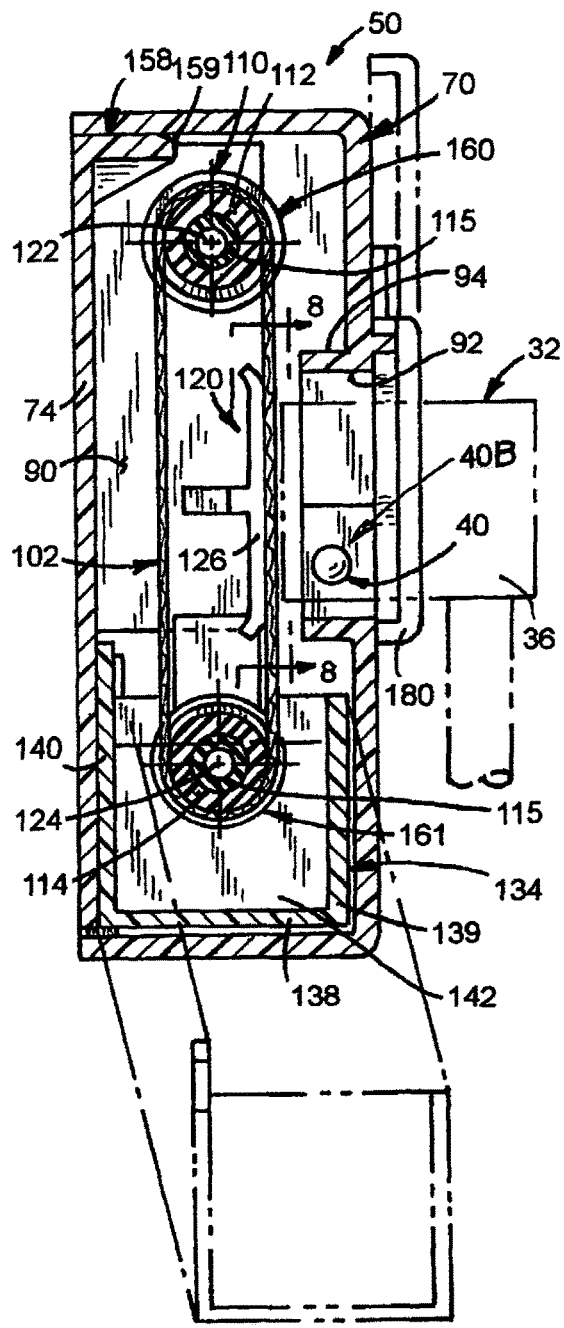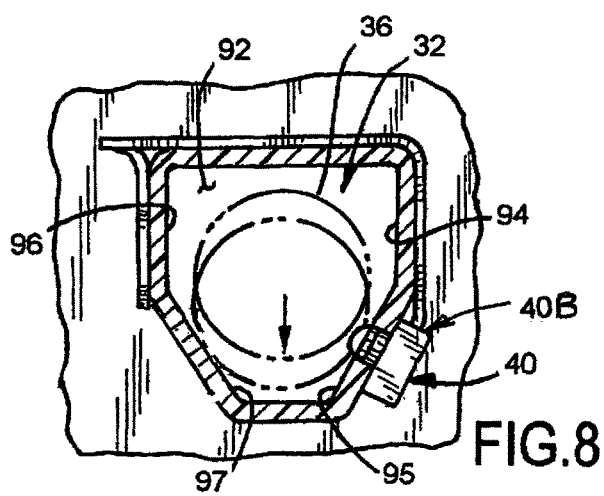

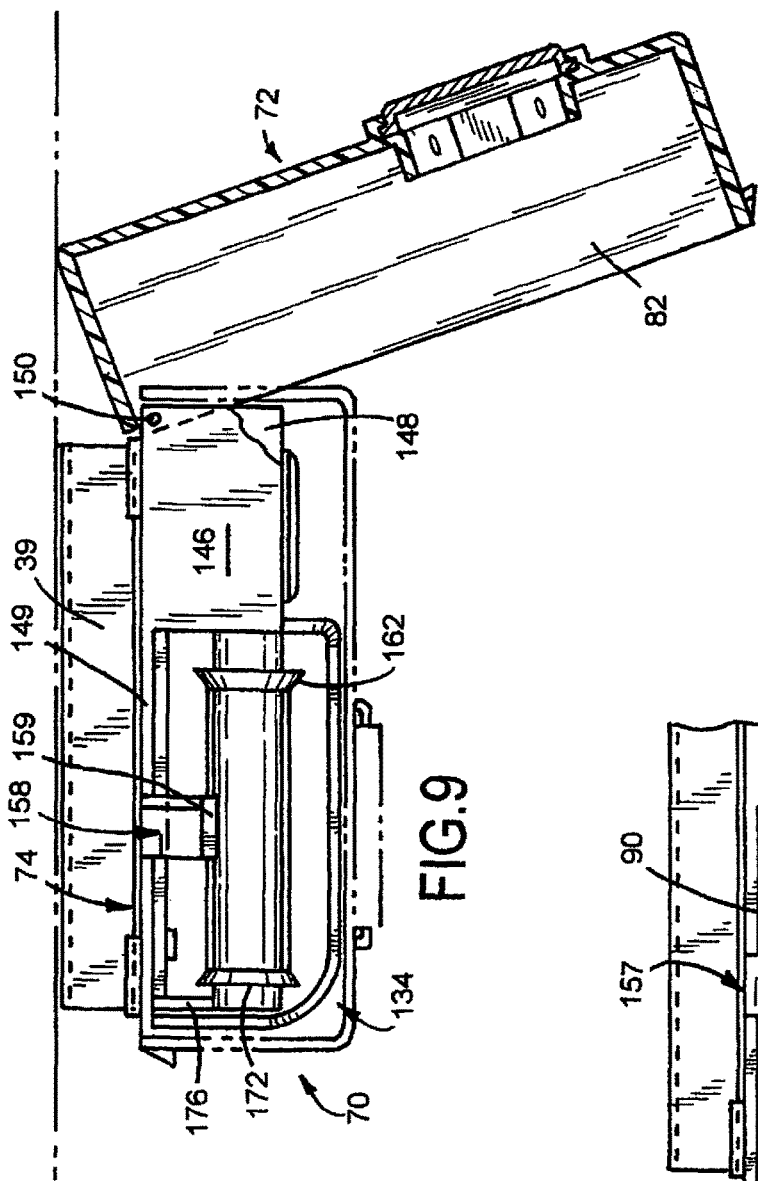
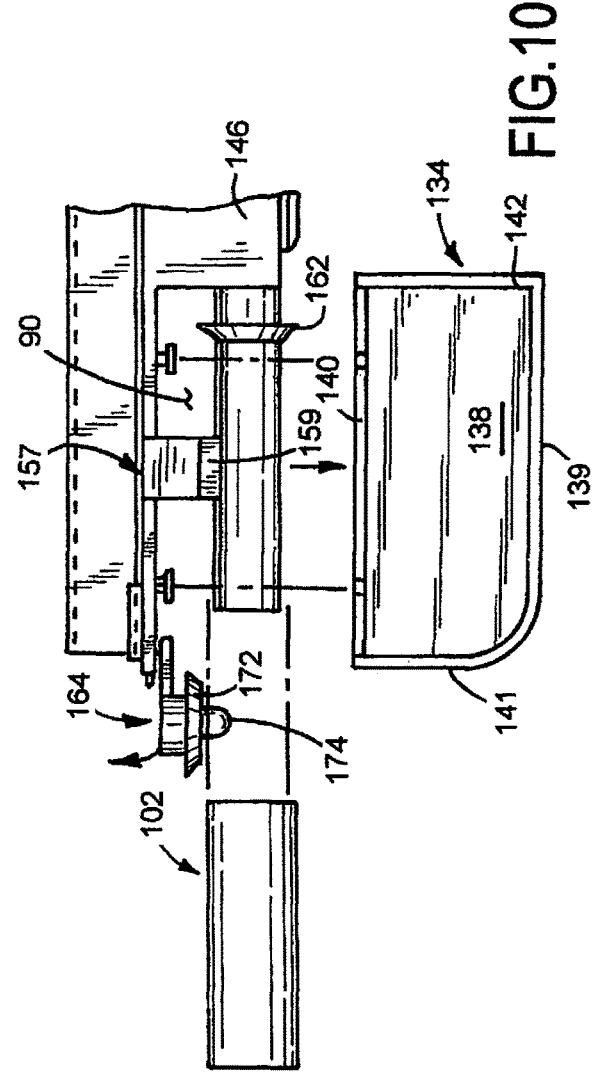

SYSTEM FOR MONITORING CLEANING EFFORTS OF CAREGIVERS USING STETHOSCOPES

RELATED APPLICATION

This application is a Continuation-In-Part to U.S. patent application Ser. No. 14/868,749, filed Sep. 29, 2014, now U.S. Pat. No. 9,949,713 entitled SYSTEM FOR MONITORING CLEANING EFFORTS OF CARE GIVERS USING STETHOSCOPES, the entirety of which is incorporated by reference herein.

FIELD OF THE INVENTION DISCLOSURE

The present invention disclosure relates to a system for monitoring cleaning efforts of care givers using stethoscopes.

BACKGROUND OF THE INVENTION DISCLOSURE

More than one million people get sick each year from infections they contract in hospitals. This has resulted in as many as 100,000 deaths. Fighting these infections costs the healthcare system about $30 billion dollars every year. These statistics are just for hospitals in America. The number of people affected and costs worldwide are considerably greater.

Significant advances have been and are continuing to be made in the field of medical technology. An important and invaluable medical tool to health care providers including doctors, nurses and technicians and which is used in connection with and has lead to such advances is a stethoscope having a head or chest portion. Care givers routinely use stethoscopes to facilitate a patient's medical care by examining the chest, abdomen, and other areas of the patient. Patients in hospitals and related medical facilities often require a greater extent of medical care such as surgery and related invasive procedures which can often leave open wounds. The bodily fluids secreted from such open wounds may be contaminated with infectious agents, including viruses such as human immunodeficiency virus (HIV) thereby resulting in possible contamination of the head portion of the stethoscope.

Multiple types of stethoscopes are commonly used by care givers or health care providers. A care giver can use an inexpensive stethoscope that is typically disposed of after each use such as in intensive care units (ICU's and the like) or ward where VRE (Vancomycia Resistant Enterococcus) or MRSA (Methacillia Resistent Staph, Aureus) and related infections are commonly located. Such disposable stethoscopes, however are usually ill fitting to the care giver, poor quality, and often inadequate for detecting subtle human abnormalities. Electronic stethoscopes are also known in the art. Moreover, most physicians and nurses prefer to use their own individual stethoscope. As used herein and throughout, the term or phrase "stethoscope" is intended to include all such types of instruments used to detect and study sounds produced in a body.

A risk of spreading infections with a stethoscope exists because of its routine use by health care providers throughout the day on multiple patients. Although care givers work with only the best intentions of the patient as their paramount concern, often times and whether by inadvertence or laziness, a care giver will use a stethoscope on one person/patient and, then, reuse the same stethoscope without specific cleaning and sanitation measures being effected between patients. To inhibit the spread of infection, some care givers will wipe the head portion of the stethoscope with an alcohol swab between patients. Such cursory cleaning and sanitization efforts, however, are often inadequate to completely destroy infectious contaminants on the diaphragm of a stethoscope and are often infrequently used between persons/patients. Also, the design of some stethoscopes makes effective wiping of the head or chest portion thereof difficult.

As will be appreciated, medical emergencies only serve to exacerbate these problems. Often times, care givers simply do not have the time necessary and required to adequately clean and sanitize the head or chest portion of their stethoscope between persons/patients. Moreover, and during rounds, doctors are required to frequently pass from one patient's room to another and yet are expected to have enough time to thoroughly and carefully examine each patient. Reusing the stethoscope without sufficient and cleaning and sanitization care being provided thereto often results in the inadvertent but yet positive transference of nosocomial infection or cross contamination between persons/patients.

Thus, there is a need and continuing desire for a system for monitoring cleaning and sanitization efforts of health care givers/providers using stethoscopes.

SUMMARY

In view of the above, and in accordance with one aspect of this invention disclosure, there is provided a system for monitoring cleaning efforts of care givers using stethoscopes. According to this aspect, such a system includes one or more cleaning stations capable of cleaning a head portion of a stethoscope presented thereto. The cleaning stations form part of a network used to monitor cleaning efforts of care providers/givers using stethoscopes. Each cleaning station includes a housing and cleaning apparatus disposed within the housing, with the cleaning apparatus being structured to clean a head portion of a stethoscope presented thereto. The system also includes an identification apparatus operably associated with and assigned to each one of a plurality of stethoscopes for identifying each particular stethoscope. The identification apparatus has a specific code identifying a particular stethoscope and, thus, a particular health care provider. In one form, a first apparatus is provided for detecting, developing and sending a signal each time the identification apparatus operably associated with a particular stethoscope is disposed within a predetermined radius of a cleaning station. A second apparatus is provided for detecting, developing and sending a signal each time the identification apparatus operably associated with a particular stethoscope is presented to a cleaning apparatus of one of the cleaning stations to effect a cleaning event. A networked database system is integrated with each cleaning station. The database system includes an analysis unit operably responsive to the signals received from the first apparatus and the second apparatus for calculating the cleanliness level of each particular stethoscope having the identification apparatus operably associated therewith.

As used throughout, and as will be appreciated, the "cleanliness level" of a particular stethoscope can be evaluated using a number of different factors. One of the factors used in determining the "cleanliness level" of a particular stethoscope can include, but is not limited to, the number of cleaning events each particular stethoscope is subjected to during a given period of time. Another factor used in determining the "cleanliness level" of a particular stethoscope can include, but is not limited to, the exposure of each stethoscope to either a patient or person to whom care is being provided. Another factor used in determining the "cleanliness level" of a particular stethoscope can include, but is not limited to, the duration or time period each particular stethoscope is presented to a cleaning apparatus of one of the cleaning stations for a cleaning event. Still another factor used in determining the "cleanliness level" of a particular stethoscope following a cleaning event can include the cleaning medium used to clean the stethoscope. Any number of additional factors can be used and calculated by the analysis unit of this invention disclosure to determine and evaluate the "cleanliness level" of a particular stethoscope.

In this regard, and according to this aspect of this invention disclosure, the system for monitoring cleaning efforts of care givers using stethoscopes furthermore preferably includes recording each cleaning event only after the second apparatus detects the presence of the cleaning head of a particular stethoscope within a specified range of one of the cleaning stations for a predetermined time period. Moreover, the system for monitoring cleaning efforts of care givers using stethoscopes preferably includes a network repository configured to store information received from each cleaning system and the analysis unit regarding the presence of a particular stethoscope being detected by either the first apparatus and/or the second apparatus at any cleaning station.

In a preferred embodiment, the networked database system for the system for monitoring cleaning efforts of care givers using stethoscopes further includes a monitoring apparatus operably connected to the analysis unit for taking into account actual usage of any one of the stethoscopes having the identification apparatus operably associated therewith and configured to develop data indicative of a wearing event for each stethoscope. In this regard, the "cleanliness level" of each stethoscope is at least partially determined by the data generated by the monitoring apparatus.

According to another aspect, there is provided a system for monitoring cleaning efforts of care givers using stethoscopes including a plurality of cleaning stations disposed at different locations throughout a facility. Each cleaning station is capable of cleaning a head portion of a stethoscope presented thereto. In this embodiment, each cleaning station includes a housing and a cleaning apparatus disposed within the housing. An identification apparatus is operative to identify an individual stethoscope in a group of stethoscopes. A far field antenna is operably associated with each cleaning station. The far field antenna operably associated with each cleaning station is designed and configured to detect, develop and send a signal each time the identification apparatus associated with a particular stethoscope is disposed within a predetermined radius of a cleaning station. A near field antenna is also operably associated with each cleaning station. The near field antenna operably associated with each cleaning station is designed and configured to detect, develop and send a signal each time the identification apparatus operably associated with a particular stethoscope is presented to a cleaning station to effect a cleaning event. An analysis unit is configured to compute data and signals from said near field and far field antennas of each cleaning station and calculate a duration of each cleaning event that has happened to an identified stethoscope at any of said cleaning stations and determine the "cleanliness level" of each stethoscope having the identification apparatus attached thereto partly as a function of the number of cleaning events for each identified stethoscope at one or more of the cleaning stations compared against a fixed value.

In this embodiment of the invention disclosure, each cleaning event is recorded after the near field antenna senses the presence of the cleaning head of a particular stethoscope relative to one of the cleaning stations for a predetermined time period. Preferably, the system for monitoring cleaning efforts of care givers using stethoscopes further includes a network repository configured to store information received from the analysis unit regarding the presence of a particular stethoscope being detected by either the far field antenna or the near field antenna of any cleaning station. In a preferred embodiment, the repository is configured to store information regarding each time a particular stethoscope is presented within the predetermined radius of one of the cleaning stations.

In one embodiment, the system for monitoring cleaning efforts of care givers using stethoscopes further includes an apparatus operably connected to the analysis unit and operative to monitor a wearing event for each stethoscope. As such, the cleaning efforts for a particular stethoscope are partially evaluated as a function of the number of wearing events detected by the apparatus for monitoring wearing events. Preferably, the system for monitoring cleaning efforts of care givers using stethoscopes further includes an apparatus operably connected to the analysis unit for displaying an indication of the cleanliness of a particular stethoscope. The identification apparatus operably associated with each stethoscope in the group of stethoscopes includes an RFID device.

Optionally, there is provided a system for monitoring cleaning efforts of care givers using stethoscopes including one or more cleaning stations. Each station includes a cleaning apparatus disposed within a housing and structured to clean a head portion of a stethoscope presented thereto. An identification apparatus is operably associated with each of a plurality of stethoscopes for identifying each particular stethoscope. A far field antenna is operably associated with each cleaning station. The far field antenna is designed and configured to detect, develop and send a signal each time the identification apparatus associated with a particular stethoscope is disposed within a predetermined radius of a cleaning station' Also, a near field antenna is operably associated with each cleaning station. The near field antenna on each cleaning station is designed and configured to detect, develop and send a signal each time the identification apparatus operably associated with a particular stethoscope is presented to a cleaning station to effect a cleaning event. Moreover, and according to this aspect of the invention disclosure, the system for monitoring cleaning efforts of care givers using stethoscopes further includes an apparatus configured to generate a signal indicative of whether a particular stethoscope having an identification apparatus operably associated therewith is timely presented to an adjacent cleaning station for a cleaning event, and wherein the timely presentation of the particular stethoscope to be cleaned requires the particular stethoscope to be presented to the cleaning apparatus of a cleaning station within a predetermined period of time following the far field antenna detecting when a particular stethoscope having an identification apparatus operably associated therewith comes within a specified radius of a cleaning station. According to this feature of the invention disclosure, the networked analysis unit is configured to compute data and signals from both the near field and far field antennas of each cleaning station and is configured to calculate the "cleanliness level" of each particular stethoscope having the identification apparatus operably associated therewith.

According to this aspect of the invention disclosure, the system for monitoring cleaning efforts of care givers using stethoscopes allows each cleaning event to be recorded after the near field antenna senses the presence of the cleaning head of a particular stethoscope relative to one of the cleaning stations for a predetermined time period. Optionally, the system for monitoring cleaning efforts of care givers using stethoscopes further includes a networked repository configured to store information received from the analysis unit regarding the presence of a particular stethoscope being detected by either the far field antenna or the near field antenna. The repository is configured to store information regarding each time a particular stethoscope is presented within the predetermined radius of one of the cleaning stations.

Preferably, the system for monitoring cleaning efforts of care givers using stethoscopes further includes an apparatus operably connected to the analysis unit and operative to monitor a wearing event for each stethoscope. As such, the cleaning efforts for a particular stethoscope can be partially evaluated as a function of the number of wearing events detected by the apparatus for monitoring wearing events. Optionally, the system for monitoring cleaning efforts of care givers using stethoscopes can further includes an apparatus operably connected to the analysis unit for displaying an indication of the cleanliness of a particular stethoscope.

According to still another aspect of this invention disclosure there is provided a method for monitoring cleaning efforts of care givers using stethoscopes. Such method includes the steps of: establishing a relationship between a care giver and a particular stethoscope; providing a cleaning station capable of cleaning a head portion of a stethoscope presented thereto for cleaning; detecting and signaling when each individual stethoscope comes within a predetermined radius of a cleaning station; detecting and signaling when each individual stethoscope is presented to a cleaning station for a cleaning event; and, analyzing the "cleanliness level" of each stethoscope.

Optionally, the method for monitoring cleaning efforts of care givers using stethoscopes includes the further step of: recording when each particular stethoscope is presented to a cleaning station for a cleaning event only after each particular stethoscope is presented to a cleaning station for a predetermined period of time. Preferably, the method for monitoring cleaning efforts of care givers using stethoscopes also includes the further step of: storing in a network repository each time a particular stethoscope is presented to the cleaning station for a cleaning event. A preferred method for monitoring cleaning efforts of care givers using stethoscopes comprises the further step of: monitoring wearing events for each stethoscope, and wherein each cleaning effort is partly evaluated according to the number of monitored wearing events. A preferred method for monitoring cleaning efforts of care givers using stethoscopes comprises the further step of: comparing the number of cleaning events for a particular stethoscope against a predetermined value to determine the cleanliness level of each particular stethoscope.

BRIEF DESCRIPTION OF THE DRAWINGS

FIG. 2 is a perspective view showing one example of a cleaning station forming part of the system for monitoring cleaning efforts of care givers using conventional stethoscopes;

FIG. 3 is an enlarged side elevational view of the cleaning station illustrated in FIG. 1 attached to a suitable support surface and showing a stethoscope about to be inserted to effect a cleaning event;

FIG. 6 is an enlarged cross-sectional view taken along line 6-6 of FIG. 4;

FIG. 7 is a cross-sectional view taken along line 7-7 of FIG. 4 and illustrating a head portion of the stethoscope inserted for a cleaning event in the cleaning station;

FIG. 8 is an enlarged cross-sectional view taken along line 8-8 of FIG. 7;

FIG. 9 is a top plan view with a cover of the cleaning station shown in section and moved to a position to show an interior of the cleaning station;

FIG. 10 is a fragmentary view similar to FIG. 9 but showing various components of the cleaning station in disassembled relation relative to each other;

DETAILED DESCRIPTION

Figure 1:
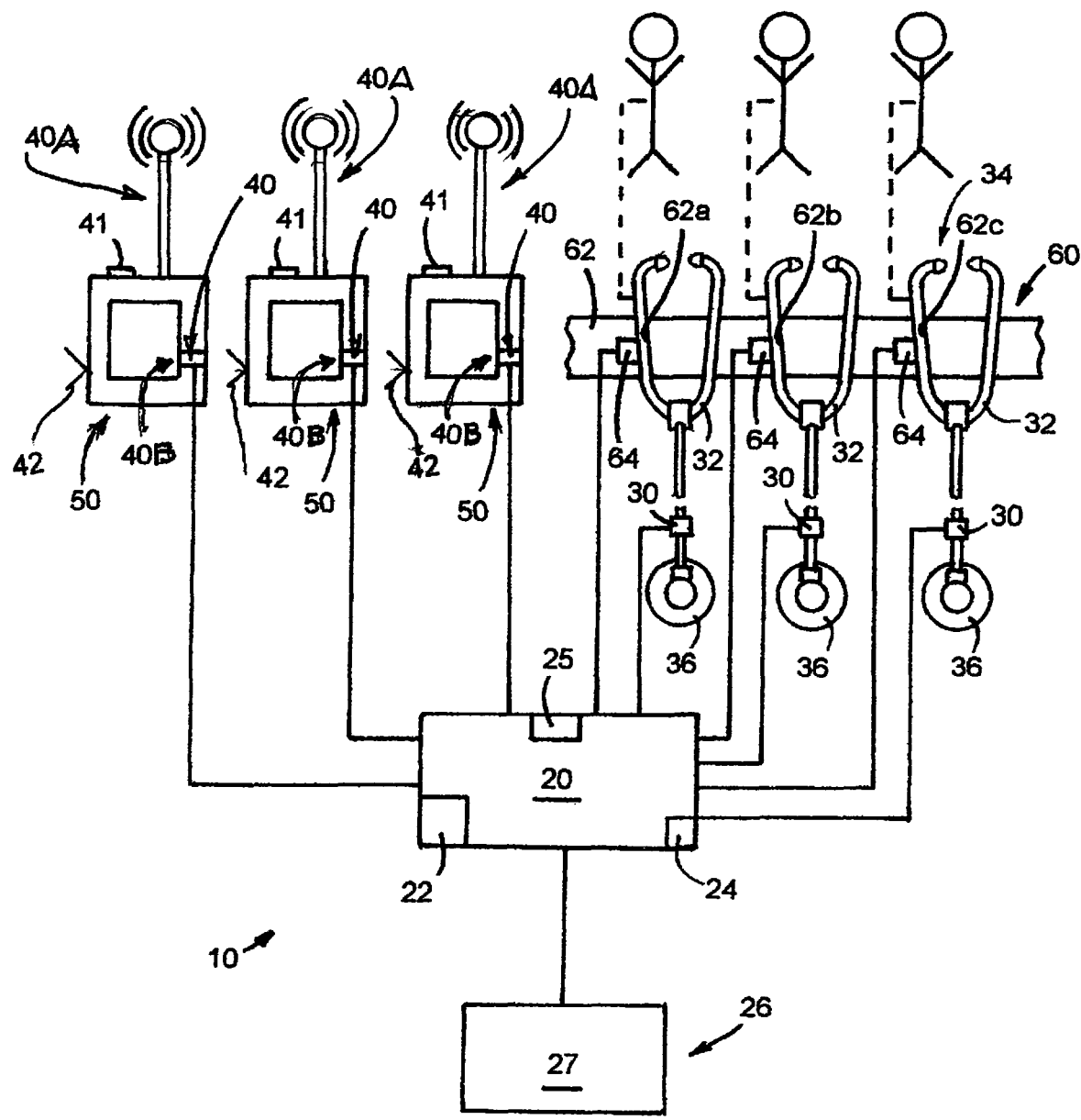
FIG. 1 is a schematic illustration of one embodiment of a system for monitoring cleaning efforts of care givers using conventional stethoscopes.

The following detailed description is directed to a system and method for monitoring cleaning and sanitization efforts of care givers using stethoscopes. As described briefly above, nosocomial and related infections are a significant concern to hospitals, emergency care facilities, doctor's offices and other patient care facilities around the world. In many cases, nosocomial and related infections may be controlled through the establishment of and adherence to proper sanitization procedures, including cleaning and sanitization of stethoscopes.

Utilizing the concepts and technology disclosed herein, a system for monitoring cleaning efforts of care givers using stethoscopes in patient care facilities is provided whereby enhancing opportunities for those care givers using stethoscopes to become more aware of the cleanliness levels of such medical devices and equipment. As will be explained in greater detail below, and in some embodiments of this invention disclosure, reports can be generated to identify the care giver and/or health care provider who have not taken those positive steps to ensure the cleanliness levels of their stethoscope.

By utilizing various aspects of the invention disclosure provided below, health care personnel can be reminded when they need to clean their stethoscope. By utilizing various aspects of this invention disclosure provided below, reports can be generated alerting others to the level of cleanliness care being effected by such individuals. Patients are thereby provided with significantly enhanced protection against infections being inadvertently being transferred between patients through use of contaminated stethoscopes. It should furthermore be appreciated various embodiments of this invention disclosure can be used in any of several different environments, i.e., hospitals, doctors's offices and other patient care environments which would all undoubtedly receive a tremendous benefit from preventing the spread of germs via simple cleaning of the stethoscopes used therein.

While this invention disclosure is susceptible of embodiment in multiple forms, there is shown in the drawings and will hereinafter be described preferred embodiments, with the understanding the present disclosure is to be considered as setting forth exemplifications of the invention disclosure which are not intended to limit the disclosure to the specific embodiments illustrated and described.

Referring now to the drawings, wherein like reference numerals indicate like parts throughout the several views, there is schematically illustrated in FIG. 1 a system, generally indicated by reference numeral 10, for monitoring cleaning efforts of care givers using conventional stethoscopes. Optionally, system 10 both operably tests the compliance of care givers using stethoscopes with given standards and tests the quality of the cleaning of the stethoscopes used by such healthcare providers. In one form, system 10 includes a networked analysis unit 20 which preferably includes a suitable programmable computer 22 including a processor 24. Optionally, the analysis unit 20 further includes a network repository 25 for storing each time a particular stethoscope 32 in a group of stethoscopes 34 is presented for a cleaning event. Moreover, the analysis unit 20 can be structured and programmed to perform an analysis of the cleaning efforts of any one or a plurality of healthcare providers based on a number of factors including, but not limited to: time logs of the healthcare providers; logged cleaning events; statistical analysis of recorded cleaning events; a comparison, optionally statistical, of recorded stethoscope cleaning events of others, and, any one or more related dynamic factors which may be considered important to the cleanliness level of any one or more stethoscopes.

The analysis unit 20 is operably connected to and receives data from one or a plurality of personal identification devices 30. Each personal identification apparatus 30 is operably associated with a particular stethoscope 32 in the group of stethoscopes 34. In turn, each stethoscope 32 is related to or associated with a certain person/user, such as a care giver, for example a nurse, a physician, a paramedic, a researcher, a member of a emergency medical service, and etc. whereby establishing a relationship between a care giver/health care provider and a particular stethoscope 32 in the group of stethoscopes 34.

System 10 further includes an apparatus 26 operably connected and responsive to the analysis unit 20 for providing an indication of the cleanliness level to the person/care giver associated with each respective stethoscope based on the number of factors some of which were listed above. Optionally, such apparatus 26 includes a suitable printer device 27 for printing or otherwise providing an indication of the cleanliness level of any particular stethoscope in the group of stethoscopes 34.

Each identification apparatus or device 30 is operative to identify both a person/care giver and a particular stethoscope 32 in the group 34 of conventional stethoscopes. As schematically illustrated in FIG. 1, and as is conventional, each stethoscope 32 includes a head portion 36. Optionally, each identification apparatus or device 30 can be in the form of a tag or the like having a readable code imprinted or otherwise provided thereon and wherein such code identifies a particular stethoscope 32 as well as the care giver/healthcare provider to whom the particular stethoscope is assigned. In another form, the identification apparatus 30 operably associated with each stethoscope 32 includes an apparatus for providing an electronically and automatically readable signature indicative of the identity of the stethoscope and, thus, the person to whom the stethoscope is assigned.

Optionally, such identification apparatus 30 can be in the form of an RFID (Radio Frequency Identification) tag, a tag having a magnetic strip, an Optical Character Recognition (OCR) smart card, or other suitable device for automatically providing a personal identification characteristic of the stethoscope and the person to whom the stethoscope is assigned and which allows data to be automatically collected and delivered to the analysis unit 20 for further evaluation and consideration. While only three stethoscopes 32 in the group of stethoscopes 34 are illustrated for exemplary purposes, it will be appreciated, the present invention disclosure is equally applicable and adaptable to a system and/or network for monitoring cleaning efforts of tens if not hundreds of care givers; with each care giver being personally assigned to a particular stethoscope.

In one form, the analysis unit 20 is operably connected to a detection apparatus or mechanism 40 arranged in operable combination with each of one or more cleaning units or stations 50 arranged or disposed at different locations throughout a facility. The detection mechanism 40 on each cleaning station 50 operates in combination with the identification apparatus 30 and is operative to determine both the identity of each particular stethoscope 32 and whether any particular stethoscope warrants having a cleaning event to be performed thereon. More specifically, the detecting apparatus 40 operates in operable combination with the analysis unit 20 to automatically detect each time the identification apparatus 30, attached and assigned to a particular stethoscope: 1) is presented within a predetermined radius of a cleaning station 50; and, 2) is presented to the cleaning station 50 for a cleaning event after being presented within a predetermined radius of a cleaning station 50. Preferably, the detection mechanism 40 operates in operable combination with the analysis unit 20 to detect the duration of the cleaning event during which an individual or personal stethoscope 32 is presented for a cleaning event to one of the cleaning and sanitization stations 50.

It will be appreciated, the number of cleaning stations 50 arranged in combination with and forming a part of system 10 will be dependent upon the size of the facility wherein system 10 is utilized. For example, a doctor's office may require only one or limited number of cleaning stations 50. On the other hand, a hospital or other relatively large facility can require many more cleaning stations 50 to be formed as part of system 10. Suffice it to say, the system 10 of this invention disclosure is networked so it can be equally applicable and adaptable to a monitoring system having a single and/or hundreds of cleaning stations arranged as part thereof.

The analysis unit 20, the identification apparatus 30 associated with each stethoscope 32 in the group of stethoscopes 34, and the detection apparatus or mechanism 40 forming part of system 10 all preferably communicate through a conventional wired network, for example a local area network (LAN) and wide area network (WAN), or a wireless network, for example a wireless LAN (WLAN) and/or a wireless personal area network (WPAN).

As mentioned, a detection apparatus 40 is arranged in operable combination with each cleaning unit or station 50 arranged or disposed at different locations throughout the facility, i.e., proximate each patient's room or each examination room in a facility. In one form, the detection apparatus 40 and cleaning station or unit 50 can be arranged in close proximity to the patient/person receiving care such that the person receiving such care can see and appreciate the health care worker is cognizant of the risks involved with the possibility of an inadvertent transference of infections and is taking positive steps to clean their stethoscope.

As mentioned, the detection apparatus 40 at each cleaning station 50, in whatever form, is operative to identity the time and date each stethoscope 32 having an identification apparatus 30 arranged in operable combination therewith is presented within a predetermined radius of any one of the cleaning stations 50 forming part of system 10. As discussed further below, the detection apparatus 40 at each cleaning station 50, in whatever form, is furthermore operative to detect the time and date a particular stethoscope having an identification apparatus arranged in operable association therewith is presented to that cleaning station 50 for a cleaning event to be performed thereon, and, optimally, the duration of such cleaning event.

Figure 5:
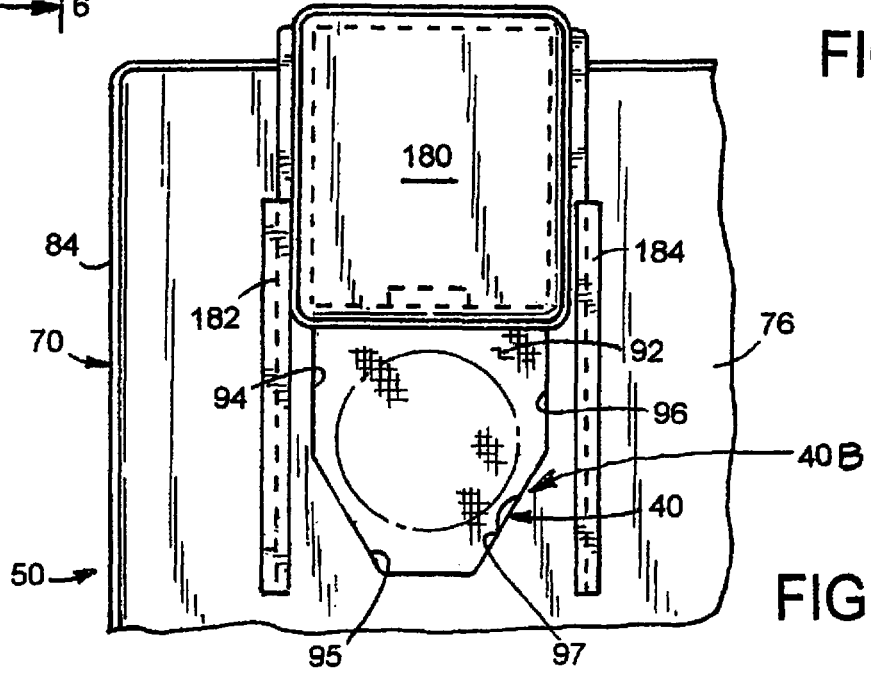
FIG. 5 is an enlarged fragmentary front elevational view taken along line 5-5 of FIG. 3.

In a preferred embodiment, the detection apparatus 40 includes a first detecting apparatus or far field antenna 40A as well as a second detecting apparatus or near field antenna 40B (FIGS. 1 and 3, 5 and 8, respectively). In one form, the far field antenna 40A is of the type sold by Nearson, Inc. under Model No. S463AM-915. Preferably, the far field antenna 40A is a flexible whip, straight RF antenna which operates in about a 902 MHz to about 928 MHz range. As illustrated in FIGS. 1, 2 and 3, the far field antenna 40A is carried on a housing 70 (FIGS. 2 and 3) of each cleaning station 50. In one form, the near field antenna 40B is of the type sold by SkyeEek as an RFID HF antenna for RFID systems in the HF frequency band of about 13.56 MHz. As illustrated in FIG. 5, the near field antenna 40B is carried on a housing 70 of each cleaning station 50. The first detecting apparatus or far field antenna 40A is operative to detect and develop a signal delivered to the analysis unit 30 when, including date and time, one or more care givers with stethoscopes having an identification apparatus 30 operably associated therewith is/are presented within a predetermined radius of any one of the cleaning stations 50 forming part of system 10. That is, when one or more care givers with stethoscopes having an identification apparatus 30 operably associated therewith walk into a hospital/examining room, the first detecting apparatus or far field antenna 40A is operative to detect and develop a signal delivered to the analysis unit 20 indicative of the particular stethoscopes entering the room. The second detecting apparatus or near field antenna 40B is operative to detect and develop a signal delivered to the analysis unit 30 regarding the time and date a particular stethoscope having an identification apparatus arranged in operable association therewith is presented to that cleaning station 50 for a cleaning event to be performed thereon, and, optimally, the duration of such cleaning event.

Each cleaning station 50 of system 10 operably serves to clean and, preferably, disinfect the head portion 36 of the stethoscope 32 presented thereto. It should be appreciated from an understanding of the present disclosure, however, the cleaning station 50 can embody many different designs and forms without detracting or departing from the broad spirit and novel scope of this invention disclosure.

In a preferred embodiment, and to reduce energy consumption, each station 50 functions or operates in either an "operational" mode or a "stand-by" mode. Typically, each cleaning station 50 is in a "stand-by" mode of operation during which operation energy consumption is minimized. When a health care provider having a stethoscope with a identification apparatus 30 arranged in operable combination therewith comes within a specified radius of a cleaning station 50, however, the far field antenna 40A of the cleaning station enables station 50 to operate in an "operational" mode. In a preferred form, it will be appreciated, when the health care provider having a stethoscope with a identification apparatus 30 arranged in operable combination therewith leaves such predetermined radius, the cleaning station 50 automatically returns to the "stand-by" mode of operation following a predetermined time period.

In one form shown in FIG. 2, the cleaning station 50 includes a housing 70 of multi-walled construction. In one form, housing 70 includes a cover 72 mounted in releasable and sealable association with a base 74 (FIG. 3). Preferably, cover 72 and base 74 are formed from plastic or other material that is non-permeable to liquids. Cover 72 is preferably of uni-body constructions and, in the illustrated example, includes a front wall portion 76 with multiple wall portions extending rearwardly therefrom. In the illustrated embodiment, cover 72 includes top and bottom generally parallel wall portions 80 and 82, respectively, rigidly joined to opposed and generally parallel side wall portions 84 and 86, with all the wall portions 80, 82, 84 and 86 being joined to each other and extending rearwardly from the front wall portion 76.

As shown in FIG. 3, the base 74 of housing 70 is configured with suitable brackets 89 and 89' extending rearwardly therefrom for facilitating releasable attachment of housing 70 to a stationary support surface S. As will be appreciated, the brackets 89 and 89' for releasably attaching housing 70 to the support surface S can take a form other than that shown for exemplary purposes without detracting or departing from the spirit and scope of this invention disclosure. For example, apertured hangers or mating lengths of Velcro® or the like can be attached to or formed into the housing 70.

In the example shown, housing 70 defines an interior cleaning chamber 90 (FIG. 4) defined between interior surfaces 87 of the cover 72 and an interior surface 75 of the base 74. As shown in FIGS. 5 and 7, an inlet or opening 92 is preferably defined in the front wall portion 76 of housing 70. In one form, the inlet opening 92 extends between the exterior of housing 70 and the cleaning chamber 90 (FIG. 7) for allowing insertion of the head portion 36 of the stethoscope 32 into the chamber 90 for a cleaning and sanitation event to be performed thereon.

As shown by way of example in FIG. 8, opening 92 is partially defined by a pair of depending and opposed side walls 94 and 96. The side walls 94, 96 are spaced apart by a distance allowing a head portion 36 of a conventional stethoscope 32 to pass therebetween and into the cleaning chamber 90 (FIG. 6). Preferably, the side walls 94 and 96 of opening 92 are configured to positively position and support the head portion 36 of a conventional stethoscope 32 therebetween and relative to the cleaning chamber 90 without requiring any further support or assistance from a healthcare provider. That is, after the head portion 36 of a conventional stethoscope 32 is inserted into the cleaning chamber 90, gravity, along with the hanging weight of the remainder of the stethoscope, causes the stethoscope head portion 36 to move toward a lower end of the opening 92. As the stethoscope head portion 36 moves downward under gravity toward a lower portion of the opening 92, the walls 94, 96 of opening 92 are specifically configured to isolate and support the head portion 36 of the stethoscope within the chamber 90.

In the embodiment shown by way of example in FIG. 8, the side walls 94 and 96 partially defining opening 92 preferably have a V-shaped configuration extending along at least a portion of their lengths for positively guiding and positioning the head portion 36 of the stethoscope 32 relative to the cleaning chamber 90 (FIG. 6). The side walls 94 and 96, defining opposed sides of opening 92, preferably define camming surfaces 95 and 97 extending along at least a lengthwise portion of the respective side wall 94 and 96 for positively guiding and positioning the head portion 36 of the stethoscope relative to the cleaning chamber 90. Moreover, the side walls 94 and 96 of opening 92 preferably extend rearwardly from the front wall portion 76 of housing 70 and into the cleaning chamber 90 for promoting support of the stethoscope head portion 36 inserted into the chamber 90 for effecting a cleaning event without requiring independent support assistance from a health care provider or others.

In the illustrated embodiment of station 50, a cleaning mechanism 100 is arranged in chamber 90 of housing 70 for cleaning the head portion 36 of the stethoscope 32 inserted through opening 92. It should be appreciated from an understanding of the present disclosure, the cleaning mechanism 100 can come in many different designs and forms without detracting or departing from the broad spirit and novel scope of this invention disclosure. In the embodiment illustrated by way of example in FIG. 6, the cleaning mechanism 100 includes a cleaning member 102 of resilient material such as cloth which tends to absorb and hold, liquid and, yet, will not scratch or abrade the face of the head portion 36 of the stethoscope inserted into chamber 90 for a cleaning event. In the illustrated embodiment, the resilient cleaning member 102 is positioned in chamber 90 for engagement with a face of the head portion 36 of the stethoscope after the head portion 36 of the stethoscope is inserted through the port or inlet opening 92 of housing 70.

Optionally, the resilient cleaning member 102 is configured as a belt and forms part of a rotating drive assembly 110. Drive assembly 110 further includes a pair of roller shafts 112 and 114 arranged for rotation within chamber 90 of housing 70 and about axes 122 and 124, respectively. The axes 122 and 124 extend in general parallel relation relative to each other. As shown, the cleaning belt 102 is entrained in driving relation about the shafts 112 and 114 and rotates therewith. In one form, each shaft 112, 114 has an internal throughbore or hollow core 115 (FIG. 7) opening to opposite ends of the respective shaft.

The shafts 112, 114 are preferably positioned within the chamber 90 whereby a lengthwise portion of the cleaning member 102 is positioned relative to the opening 92 such that when the head/chest portion 36 of a stethoscope is inserted through port 92 and into chamber 90 to effect a cleaning event, the cleaning member 102 engages with the head portion 36 of the stethoscope to thoroughly clean the entire head/chest portion 36 of the stethoscope from nosocomial infection and related contaminants. Member 102 is preferably impregnated with a suitable solution to clean and, preferably, disinfect the head portion 36 of the stethoscope inserted into engagement therewith. The cleaning solution can be of any suitable anti-bacterial solution which operably cleans and, preferably, disinfects a surface contacted thereby and optionally has a relatively low rate of vaporization. Cleaning solutions such as chlorhexidine or alcohol are but two types of solutions that readily lends themselves to this situation.

Optionally, a support 120 is provided for facilitating cleaning the head portion 36 of the stethoscope 30 once the stethoscope head portion 36 is inserted into chamber 90 of housing 70 for a cleaning event to be performed thereon. More specifically, and in the embodiment shown in FIGS. 4 and 7, the base 74 of housing 70 is preferably configured with a plate-like member 126 arranged to one side of the belt 102 opposite the inlet port or opening 92. The purpose of the member 126 is to support a lengthwise portion of the belt 102, opposite from the inlet opening 92, from deflecting beyond a predetermined limit in response to the stethoscope head portion 36 being placed thereagainst during a cleaning event.

Returning to FIG. 4, in the illustrated form, drive assembly 110 further includes a motor 130 for rotatably driving at least one of the shafts 112, 114 and thereby the belt 102 entrained thereabout. The motor 130 is operably connected to a suitable power source 132 which, in the illustrated embodiment, includes batteries 134 but can likewise be any common electrical power source.

Optionally, the housing 70 furthermore preferably includes a removable sump 135 for holding a supply of suitable cleaning solution therein. In the illustrated embodiment, and during operation of drive assembly 110, a lengthwise portion of the belt 102 continually passes through the sump 135 to effect a cleaning action for and to maintain the cleaning member 102 with moisture to thoroughly clean the stethoscope head or chest portion 36 during a cleaning event. The ability to quickly and readily remove the sump 135 from housing 70 facilitates frequent changing and/or replacement of the cleaning solution within the sump 135. As such, the cleaning solution in the sump 135 can preferably and particularly be suited to the particular infection which may be associated with a particular person/patient being treated and/or examined.

Figure 4:
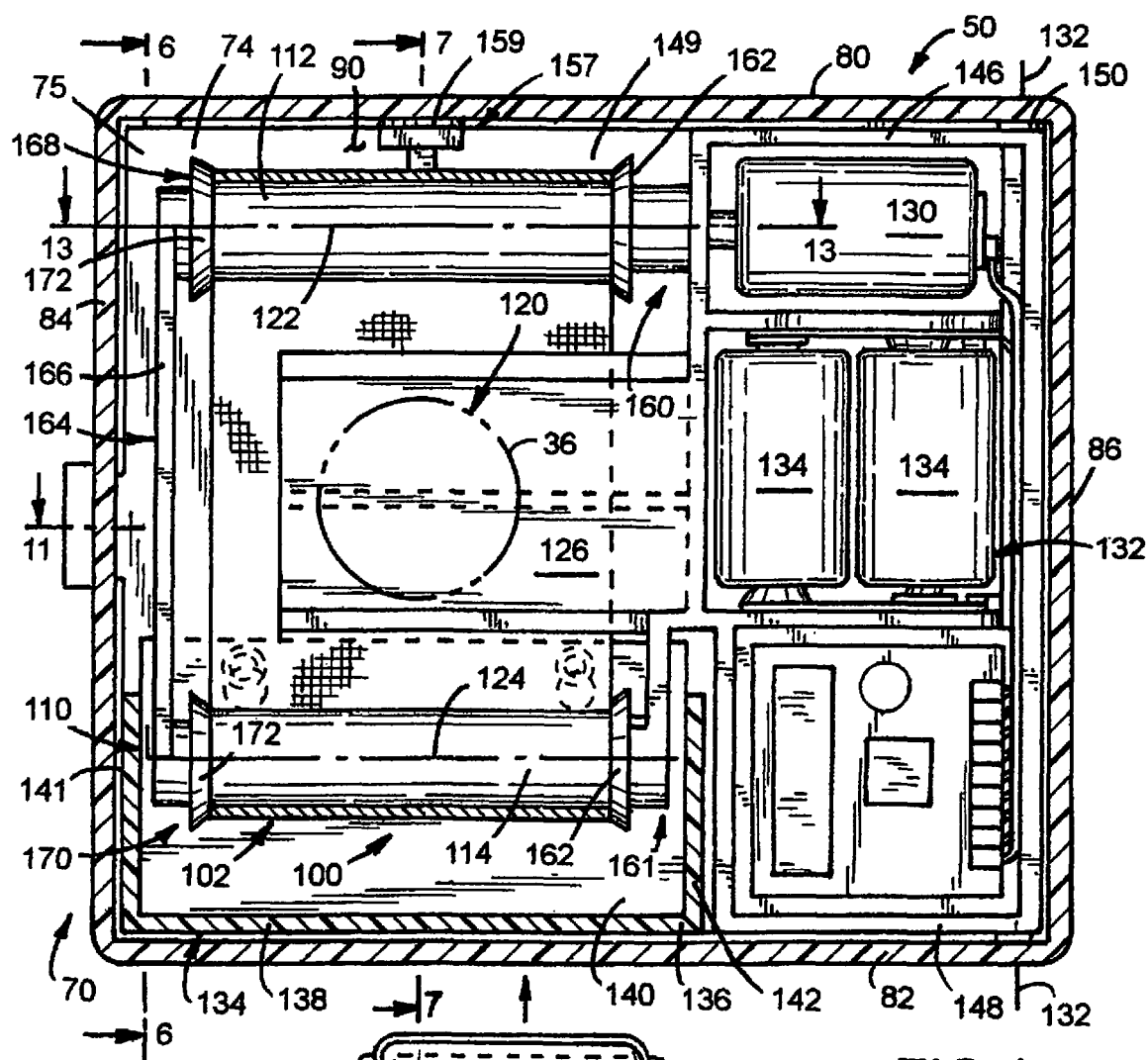
FIG. 4 is an enlarged cross-sectional view taken along line 4-4 of FIG. 3.

In the embodiment shown is FIGS. 4, 6 and 7, sump 135 preferably includes a liquid tight housing 136 for holding a supply of cleaning solution therein. In the form shown by way of example, housing 136 has a bottom wall portion 138 joined to upstanding and laterally spaced front and back wall portions 139 and 140, respectively, and longitudinally spaced end wall portions 141, 142. The wall portions of housing 136 are configured to offer a depth to the housing 136 such that sump 135 can hold a significant amount of cleaning solution therein. In one form, the back wall portion 140 is preferably configured for releasable attachment to the interior surface 75 of base 74. Suffice it to say, the sump 135 is positioned within the cleaning chamber 90 of housing 70 such that at least a portion of the belt 102 entrained about the shafts 112, 114 passes through the cleaning solution in the sump 135 during each cleaning event for the stethoscope head portion 36 whereby effecting a continuous cleaning of the belt 102.

In another form of this invention disclosure, a container for holding a significant amount of cleaning solution therein can be arranged in proximate but separate relation from each housing 70 of the cleaning unit or station 50. Suitable plumbing can be used to connect such a container to the cleaning station unit housing 70 for delivery to the cleaning mechanism 100. Moreover, housing 70 can be provided with a suitable drain which leads to a collection system arranged separate from the cleaning station housing 70 and wherein waste or used cleaning fluid is collected. As will be appreciated, this alternative version of supplying a cleaning solution to the cleaning station or unit 50 readily lends itself to using different types of cleaning solutions for guarding against inadvertent transference of different types of infections between different patients/persons whereby significantly enhancing the versatility of this invention disclosure in the treatment of different types of infectious and communicable diseases.

As mentioned above, the detection mechanism 40 (FIG. 1) is arranged for sensing and identifying, as through the identification apparatus or sensor 30 (FIG. 1), the particular stethoscope 32 in the group of stethoscopes 34 being presented to the cleaning station or unit 50 to effect a cleaning event. As mentioned, the detection mechanism 40 serves to: 1) monitor which particular stethoscope 32 in the group of stethoscopes 34 comes within a predetermined radius of the cleaning station; and, 2) monitor which particular stethoscope 32 in the group of stethoscopes 34 is presented to the cleaning or unit 50 to effect a cleaning event; and, 3) monitor when the particular stethoscope 32 in the group of stethoscopes 34 is presented to the cleaning station or unit 50 to effect a cleaning event; and 4) calculate how long the particular stethoscope 32 in the group of stethoscopes 34 is presented to the cleaning station or unit 50 to effect a cleaning event.

The detection mechanism 40 can furthermore be used to detect when a care giver/health care provider with a stethoscope having an identification apparatus 30 arranged in operable combination therewith comes within a specified radius of a cleaning station 50 so as to automatically switch the mode of operation of the cleaning station 50 from "stand-by" mode to an "operational" mode. Moreover, in a preferred embodiment, and unless a cleaning event is begun within a predetermined time period of the health car provider with a stethoscope having an identification apparatus 30 arranged in operable combination therewith coming within a specified radius of a cleaning station 50, an audible and/or visual alarm will be generated by a suitable apparatus 42 so as to alert/remind the health care provider of the need to clean and sanitize the head portion of their stethoscope. Preferably, such apparatus 42 is arranged on the cleaning station 50. Moreover, the detection mechanism 40 can preferably detect when the health care provider with a stethoscope having an identification apparatus 30 arranged in operable combination therewith exits the area of the cleaning station 50 whereby returning the cleaning station 50 to a "stand-by" mode of operation.

As will be appreciated by those skilled in the art, mechanism 40 can take different forms for effecting the desired ends. In operation, and as one function thereof, the detection mechanism 40 reads or otherwise detects the personal code operably associated with the identification sensor 30 on each particular stethoscope 32 and signals the analysis unit 20 to indicate which particular stethoscope 32 in the group of stethoscopes 34 is being presented to the cleaning station 50 to effect a cleaning event based on the personal code operably associated with the identification sensor 30 on the stethoscope 32. Moreover, and in combination with analysis unit 20, the apparatus 40B of mechanism 40 monitors and detects each time and date the head or chest portion 36 of a particular stethoscope 32 is presented for a cleaning event and signals the analysis unit 20 indicative of each time that particular stethoscope 32 is presented to the cleaning unit 50 to effect a cleaning event.

As a function of the signals delivered from mechanism 40, the analysis unit 50 can: 1) determine which particular stethoscope has been presented to the cleaning station 50 for a cleaning event; 2) readily determine whether the head/chest portion 36 of a particular stethoscope 36 has been presented to the cleaning unit 50 for a sufficient time to qualify that particular stethoscope as being subjected to a cleaning event; 3) record the time of such cleaning event for a particular stethoscope; and 4) record the date of each cleaning event for a particular stethoscope.

As mentioned, the detecting mechanism or apparatus 40 for effecting those ends described above, can take different forms from that described above without detracting or departing from the spirit and scope of this invention disclosure. For example, each cleaning unit 50 can be provided with an apparatus 41 for manually inputting information to the analysis unit 20 so as to identify the particular stethoscope 32 in the group of stethoscopes 34 being presented to the cleaning unit 50 for effecting a cleaning event. In one form, such apparatus 41 can include a manually operated key pad or the like which allows the care giver to input a particular code identifying the particular stethoscope 32 to be subjected to a cleaning event. Such code would be delivered to the analysis unit 20 for further processing.

In operation, apparatus 41 would function to: 1) identify which particular stethoscope 32 in the group of stethoscopes 34 is being presented to the cleaning and sanitization station 50 to effect a cleaning event based on the inputted personal code; 2) readily determine whether the head portion 36 of a particular stethoscope 32 has been presented to the cleaning unit 50 for a sufficient time to qualify that particular stethoscope as being subjected to a cleaning event; 3) record the time of such cleaning event for a particular stethoscope; and 4) record the date of each cleaning event for a particular stethoscope.

Each cleaning station 50 of system 10 is preferably operated at variable speeds. That is, the detection mechanism 40, in whatever form, furthermore serves to control operation of the respective cleaning station 50 as a function of when mechanism 40 detects or is otherwise operated to indicate the presence of a head portion 36 of a stethoscope being presented to unit 50 for a cleaning event. In one form, the apparatus 40B forming part of the detection mechanism 40 detects the presence of the head portion 36 of the stethoscope 32 in relation to the cleaning unit 50 and signals the motor 130 to operate the cleaning mechanism 100.

To allow service access to the cleaning chamber 90 and, thus, to the cleaning mechanism 100, cover 72 is movably attached to the base 74 of housing 70. As shown in FIGS. 4 and 9, base 74 is provided with generally parallel upper and lower flanges 146 and 148, respectively, projecting forwardly from a back plate 149 forming part of base 74. The vertical dimension separating the flanges 146 and 148 is equal to or slightly less than the vertical distance separating the top and bottom wall portions 80 and 82 (FIG. 4), respectively, of cover 72. In the illustrated embodiment, a vertically elongated pin 150 passes through the top and bottom wall portions 80 and 82, respectively, of cover 72 as well as through the upper and lower flanges 146 and 148, respectively, of base 74 thereby allowing the cover 72 to pivotally move about a generally vertical axis 152 (FIG. 4) between a closed position, shown in FIGS. 2, 4, 6 and 7, and an open position, shown in FIG. 9.

As will be appreciated, when cover 72 is in a closed position, housing 70 is substantially sealed and inhibited from having liquids escaping therefrom. To enhance the sealing capability of the housing 72 relative to base 74, housing 70 may further include suitable seals arranged about a periphery. The showing of such seals in the drawings, however, has been eliminated for reasons of simplicity.

As shown in FIG. 9, once cover 72 is swung or otherwise moved to an open position, access to the interior cleaning chamber 90 is ready achievable. Moreover, opening the cover 72 permits ready access to and, if desired, removal of a sump 135 from housing 70.

Figure 11:
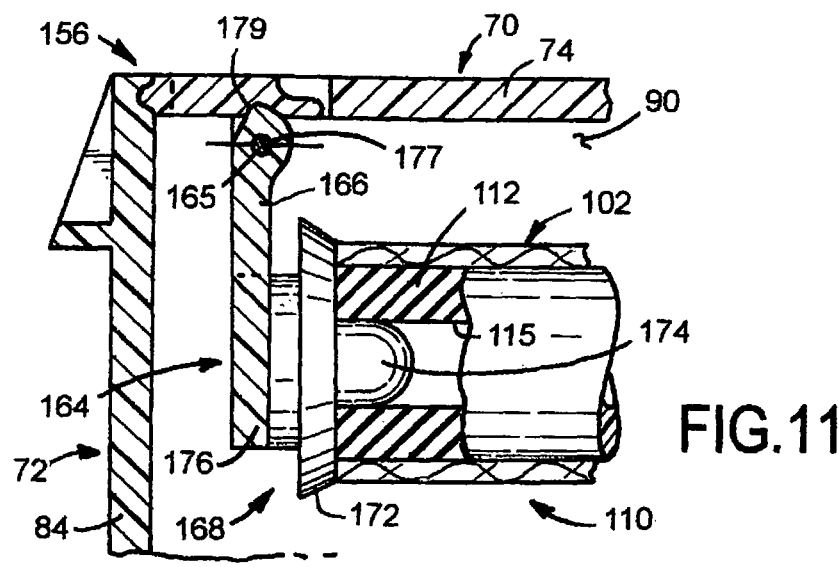
FIG. 11 is an enlarged cross-sectional view taken along line 11-11 of FIG. 4.

Preferably, and shown in FIG. 11, a suitable latch mechanism 156 releasably holds cover 72 in a releasably locked relationship with base 74. Moreover, in a preferred embodiment shown in FIGS. 4, 6, 7 and 10, base 74 is provided with a guide 157 to properly position the cover 72 relative to the base 74 when cover 72 is being closed. Guide 157 preferably has a camming surface 159 to facilitate proper positioning of the cover 72 relative to base 74.

Opening cover 72 furthermore permits access to along with repair and/or replacement of the cleaning member 102 and/or parts of the drive assembly 110. As shown in FIGS. 4 and 7, base 74 of housing 70 includes vertically spaced roller supports 160 and 161. Each roller support 160, 161 has a radially enlarged flange 162 toward one end thereof for limiting transverse movements of the belt 102 on the roller shafts 112, 114 as the drive assembly 110 is operated. The supports 160, 161 preferably provide rotational support for one end of each shaft 112, 114 of the drive assembly 110.

Opposite ends of the shafts 112, 114 are rotatably supported by a displacable support bracket assembly 164. In the embodiment illustrated by way of example in FIGS. 4, 6, 11 and 12, the support bracket assembly 164 includes a vertically rigid member 166 having two vertically spaced but substantially identical head portions 168 and 170 arranged toward opposite vertical ends thereof. As will be appreciated, in this embodiment of the cleaning unit 50, the vertical spacing between the head portions 168 and 170 on bracket assembly 164 is equal to the vertical spacing between the roller supports 160 and 161 (FIG. 4) on base 74. Each head portion 168, 170 extends away from the rigid member 166. Toward a free end thereof, each head portion 168, 170 includes a radially enlarged flange 172 similar to the flanges 162 arranged on the roller supports 160, 161, (FIG. 7). In the embodiment illustrated by way of example, the longitudinal distance separating the flanges 172 on bracket assembly 164 from the flanges 162 on the roller supports 160, 161 is generally equal to the width of the belt 102 entrained about shafts 112, 114. Like the flanges 162 on the roller supports 160, 161 the flanges 172 on the support bracket assembly 164 serve to limit transverse movements of the belt 102 during operation of the cleaning unit 50.

Figure 12:
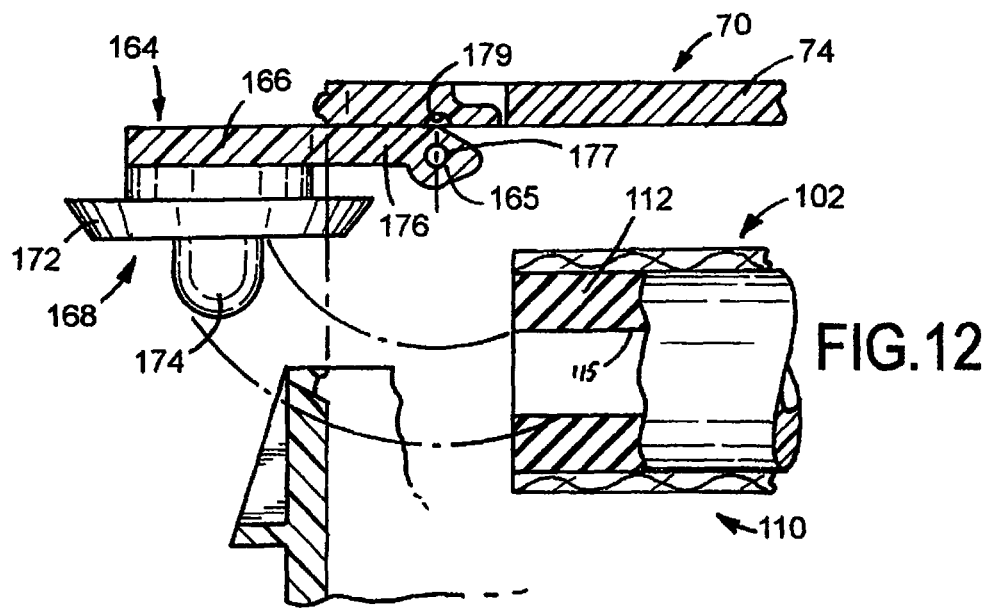
FIG. 12 is a cross-sectional view similar to FIG. 11 but showing components of the cleaning station in disassembled relation relative to each other.

Since the head portions 168 and 170 (FIGS. 4 and 6) on bracket assembly 164 are preferably identical, only head portion 168 will be further described in detail. Turning to FIGS. 11 and 12, each head portion of bracket assembly 164 furthermore preferably includes a free ended pilot 174 extending therefrom, The pilot 174 is sized to snuggly fit within the internal bore or core 115 of each roller shaft 112, 114 supported thereby. Optionally, the free end of each pilot 174 has a semi-spherical configuration to facilitate insertion of the pilot 174 into the open-ended respective core 115 of a roller shaft 112, 114 of rotating assembly 110.

In a preferred form, the support bracket assembly 164 is mounted to readily allow for repair and/or replacement of component pieces thereof. In the form illustrated by way of example in FIG. 10, the support bracket assembly 164 is configured to allow for pivotal movement thereof about a generally vertical axis 165 (FIGS. 11 and 12). In one form, the rigid member 166 of bracket assembly 164 is configured with a rigid mounting arm 176 extending rearwardly from member 166 and is pivotally joined, as by a pin 177 (FIGS. 11 and 12) defining the pivot axis 165 for the bracket assembly 164, to base 74. In one form, a suitable detent mechanism 179 between arm 176 and base 74 of housing 70 releasably maintains the bracket assembly 164 in operative position while permitting the bracket assembly 164 to be pivotally moved relative to base 74 to facilitate repair/replacement of the cleaning member 102.

Figure 13:
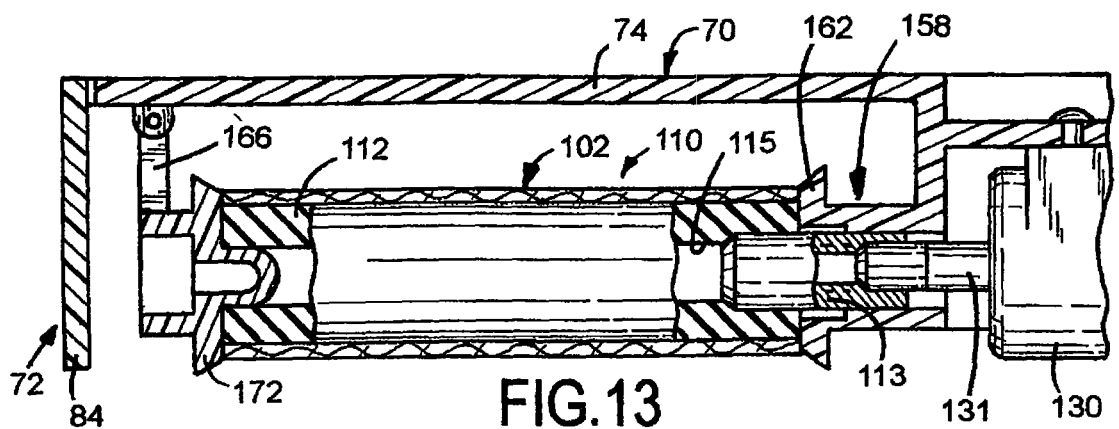
FIG. 13 is a sectional view taken along line 13-13 of FIG. 4.

In the embodiment shown in FIG. 13, drive assembly 110 is preferably driven directly from motor 130. As shown, motor 130 includes a rotatable and free ended output drive shaft 131. In one form, shaft 112 includes a generally hollow stub shaft 113 axially projecting from one end thereof. A lengthwise portion of the stub shaft 113 extends axially within the bore 115 of shaft 112 while another lengthwise portion of shaft 113 extends axially outward from the shaft 112 and into driving relationship with the distal end of the motor drive shaft 131. In one form, stub shaft 113 is journalled for rotation within the roller support 160 on base 74 of housing 70.

To promote and maintain a positive driving relationship between the roller shaft 112 and the output drive shaft 131 of motor 130, the stub shaft 113 preferably has splines axially extending from the free end thereof and along at least that portion of the shaft 113 extending within the hollow core 115 of shaft 112. In the example shown, the remaining outer diameter of the stub shaft 113, journalled for rotation within the roller support 160 on base 74 of housing 70, has a smooth outer diameter. Preferably, the distal end of the output drive shaft 131 of motor 130 also has a splined configuration extending from the free end thereof and extending within the stub shaft 113 to promote a positive driven relationship therebetween.

To inhibit contaminants from inadvertently passing into the interior cleaning chamber 90 of housing 70 through port 92, housing 70 preferably includes a manually operated and displaceable door 180 for removably closing the inlet opening 92 to chamber 90 (FIG. 5). In the embodiment illustrated by way of example in FIGS. 2 and 5, the door 180 is arranged for generally vertical displacement along a predetermined path of travel and relative to opening 92 (FIG. 5) in housing 70. In one form, the door 180 is entrapped for sliding movement between a pair of vertical tracks 182 and 184 which also serve to seal the door 180 to the housing 70 when the door 180 is in the closed position. It will be appreciated that a myriad of other designs for closing the opening 92 could be easily and readily embodied without detracting or departing from the broad spirit and novel concept of this invention disclosure.

In this embodiment of the cleaning unit 50, and when a cleaned head portion 36 of the stethoscope 32 is removed from chamber 90 of unit 50, some residual cleaning solution can remain on the head portion 36 of the stethoscope. Accordingly, and in a preferred form of cleaning unit 50, an absorbent pad 190 may be releasably and suitably attached to an exterior of housing 70. Suffice to say, the pad 190 will be formed of a suitable material that will not scratch or otherwise damage the head portion 36 of the stethoscope 32. By such construction, the healthcare provider/care giver can merely swipe the cleaned head portion 36 of the stethoscope 32 into contact with the pad 190 to remove any residual cleaning and sanitizing solution which may inadvertently remain thereon. Of course, the releasable association of the pad 190 on housing 70 facilitates disposal of the pad 190 on the housing 70 after each use to avoid inadvertent cross-contamination of the head/chest portion 36 of the stethoscope 32.

Another feature of this invention disclosure relates to the ability to control or eliminate "back contamination" of the stethoscope after the stethoscope has been used on a patient/person whereby furthermore limiting inadvertent transference of an infections between patients/persons. According to this aspect, the present invention disclosure contemplates an apparatus 192 (FIG. 3) for automatically cleaning or otherwise sanitizing the outer surfaces of each cleaning station 50 after the healthcare provider has used the stethoscope on a person/patient. In one form, apparatus 192 can include a movable device which sprays or otherwise radiates a suitable type of disinfectant toward and against the outer surfaces of the housing 70 of the cleaning station or unit 50 to effect cleaning of the outer surfaces of the housing 70. In one form, an actuation switch 194 (FIG. 3) on the housing 70 of each cleaning and sanitizing unit 50 can be used to operate apparatus 192 at a suitable time.

Figure 14:
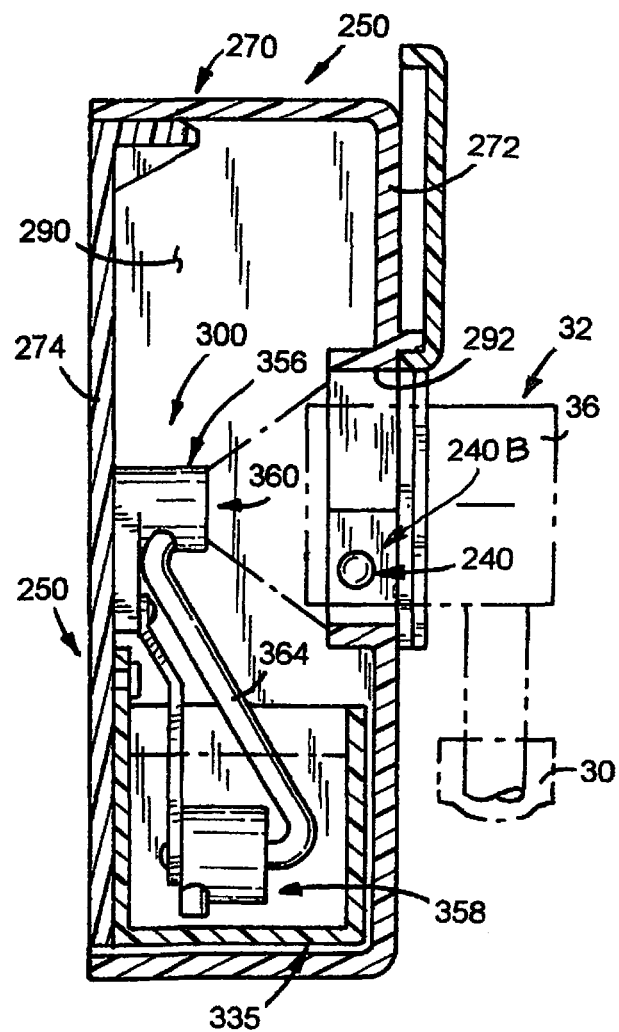
FIG. 14 is an alternative embodiment for the cleaning station.

As mentioned above, the cleaning mechanism for the cleaning unit of this invention disclosure can come in different designs without detracting or departing from the broad spirit and novel scope of this invention disclosure. In this regard, another embodiment of a cleaning station is shown in FIG. 14 and is designated generally by reference numeral 250. The elements or components of this alternative form of cleaning station that are identical or functionally analogous to those components mentioned above with respect to station 50 are designated by the reference numerals similar to those above with the exception this embodiment uses reference numerals in the 200 and 300 series.

In the embodiment shown in FIG. 14, the cleaning station 250 includes a housing 270 including a cover 272 and base 274. Suffice it to say, a head portion 36 of a stethoscope 32 is insertable into an interior chamber 290 through an inlet opening 292 provided on housing 270.

In the embodiment illustrated in FIG. 14, a cleaning mechanism 300 is arranged in the chamber 290 of the cleaning station 250. In this embodiment, the cleaning mechanism 300 includes a spray mechanism 356. The spray mechanism 356 includes a motor driven pump assembly 358 having an intake arranged in a sump 335 in the interior of housing 270 and a nozzle-like spray apparatus 360 mounted in the interior chamber 290. Preferably, and as with sump 135 described above, sump 335 is removably arranged within housing 270 for holding a supply of suitable cleaning solution therein. The ability to quickly and readily remove the sump 335 from housing 270 facilitates frequent changing and/or replacement of the solution within the sump 335. As such, the solution in the sump 135 can preferably and particularly be suited to the particular infection which may be associated with a particular person/patient being treated and/or examined.

The purpose of the spray apparatus 360 is to direct a predetermined spray pattern toward the head or chest portion 36 of the stethoscope 32 inserted through the port 292 into chamber 290 preferably with sufficient pressure to effectively and efficiently clean the head portion 36 of the stethoscope 32. It will be appreciated, that the spray pattern directed toward the head portion 36 of the stethoscope 32 is controlled such that the spray cleans the head or chest portion 36 of the stethoscope 32 while no damage is caused thereto. A suitable conduit or passage 364 operably connects the spray mechanism 356 to the pump assembly 358.

As described above, the cleaning station 250 furthermore includes a detection mechanism or apparatus 240. The detection mechanism or apparatus 240 is substantially similar regarding either embodiment of the detection mechanism or apparatus 40 described above. Moreover, the detection mechanism or apparatus 240 operates in combination with the identification apparatus 30 operably associated with each stethoscope 32 and operably serves to accomplish the same purposes and ends discussed above regarding detection mechanism or apparatus 40.

Like station 50 discussed above, the cleaning station 250 is preferably selectively operated. That is, and as described above, the near field antenna 240B of the detection mechanism 240 furthermore serves to automatically control operation of the respective cleaning station 250 as a function of when the near field antenna 240B detects or otherwise senses the presence of a head or chest portion 36 of a stethoscope being presented to unit 50 for a cleaning event. In one form, when apparatus 240B of the detection mechanism 240 detects or otherwise senses the presence of the head or chest portion 36 of the stethoscope being presented to station 250 for a cleaning event, apparatus 240B operably signals the cleaning mechanism 300 to operate for a predetermined time sufficient to effect a cleaning event on the head portion 36 of the stethoscope 32 presented to the cleaning station 250. As mentioned above, apparatus 240B can furthermore deliver a signal to the analysis unit 20 indicating the exact time and date of when any particular stethoscope having an identification apparatus 30 arranged in operable combination therewith is presented to cleaning station to have a cleaning event performed thereon.

Figure 15:
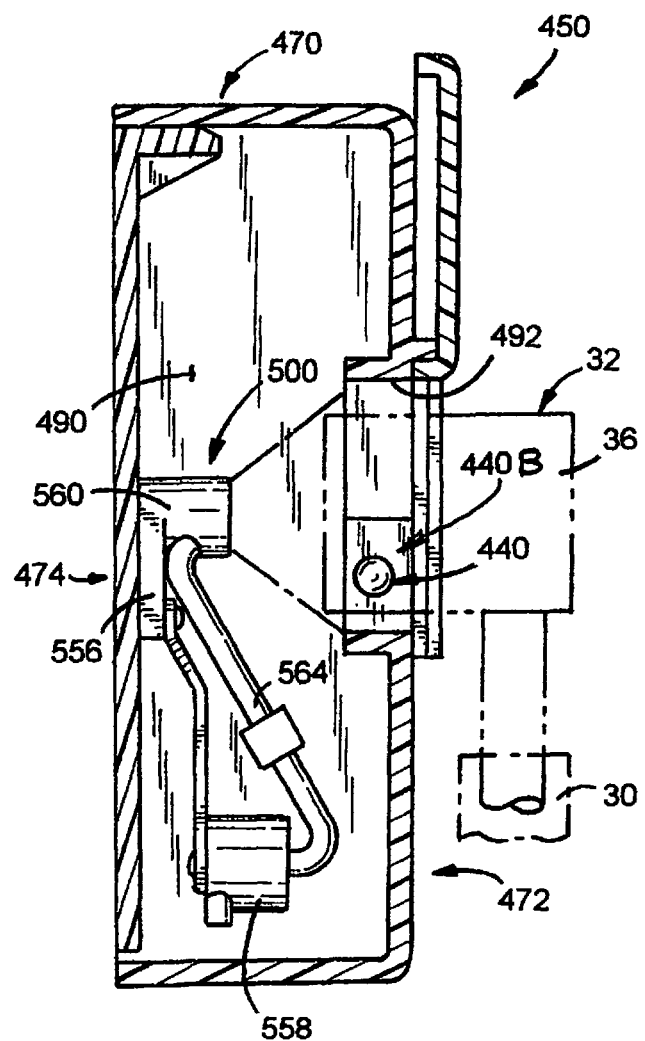
FIG. 15 is another alternative embodiment for the cleaning station.

As mentioned above, the cleaning mechanism for the cleaning unit of this invention disclosure can come in different designs without detracting or departing from the broad spirit and novel scope of this invention disclosure. In this regard, another embodiment of a cleaning station is shown in FIG. 15 and is designated generally by reference numeral 450. The elements or components of this alternative form of cleaning station that are identical or functionally analogous to those components mentioned above with respect to station 50 are designated by the reference numerals similar to those above with the exception this embodiment uses reference numerals in the 400 and 500 series.

In the embodiment shown in FIG. 15, the cleaning station 450 includes a housing 470 including a cover 472 and base 474. In this embodiment, the housing 470 is similar to housing 70 except, in this embodiment, the cover 472 and base 474 do not necessarily have to be sealed relative to each other. Suffice it to say, a head portion 36 of a stethoscope 32 is insertable into an interior chamber 490 through an inlet opening 492 provided on housing 470.

In the embodiment illustrated in FIG. 15, a cleaning mechanism 500 is arranged in the chamber 490 of the cleaning station 450. In this embodiment, the cleaning mechanism 500 includes a spray mechanism 556. The spray mechanism 556 includes a motor driven pump assembly 558 arranged in the interior of housing 470 and a nozzle-like spray apparatus 560 mounted in the interior chamber 490. Suitable plumbing 564, preferably arranged within the interior of housing 470, serves to operably interconnect the pump assembly 558 and the spray mechanism 556.

The purpose of the spray apparatus 560 is to direct a spray of air or other suitable disinfectant in whatever form in a predetermined pattern toward the head or chest portion 36 of the stethoscope 32 inserted through the port 492 into the cleaning chamber 490 with sufficient pressure to effectively and efficiently effect cleaning of the head portion 36 of the stethoscope 32. It will be appreciated, that the spray pattern directed toward the head or chest portion 36 of the stethoscope 32 is controlled such that the spray cleans the head or chest portion 36 of the stethoscope 32 while no damage is caused thereto. A suitable conduit or passage 564 operably connects the spray mechanism 556 to the pump assembly 558.

As described above, the cleaning station 450 furthermore includes a detection mechanism or apparatus 440 with a second apparatus or near field antenna 440B arranged in operable combination therewith. The near field antenna 440B is substantially similar to either embodiment described above. Moreover, the second apparatus 440B operates in combination with the identification apparatus 30 operably associated with each stethoscope 32 and serves to operably accomplish the same purposes and ends discussed above regarding either near field apparatus discussed above.

Like station 50 discussed above, the cleaning station 450 is preferably selectively operated. That is, the second apparatus 440B of mechanism 440 furthermore serves to control operation of the respective cleaning station 450 as a function of when the near field antenna 440B detects or otherwise senses the presence of a head portion 36 of a stethoscope being presented to unit 450 for a cleaning event. Preferably, when second apparatus or near field antenna 440B detects or otherwise senses the presence of the head portion 36 of the stethoscope being presented to station 450 for a cleaning event, apparatus 440B operably signals the cleaning mechanism 500 to operate for a predetermined time period sufficient to effect a cleaning event on the head portion 36 of the stethoscope 32 presented to the cleaning station 450.

Of course, it will be appreciated other forms of cleaning units could be used as part of the system 10 without detracting or departing from the spirit and broad scope of this invention disclosure. For example, the cleaning and sanitizing unit can be equipped with ultra-violet technology rather than that described in detail above for effecting a cleaning event to the stethoscope.

Optionally, this invention disclosure recognizes, appreciates and takes into consideration a care giver, i.e., a physician, nurse practitioner, nurse, researcher and etc. may not possibly be present everyday in an environment where they necessarily need to use a stethoscope. Unless this possibility, however, is taken into account and consideration, such a lapse in use of a stethoscope having a personal monitor thereon could be mistakenly interpreted as a lack of attention to cleaning of that particular stethoscope over that period of non-use. Accordingly, a preferred embodiment of this invention disclosure has been designed and developed to take into consideration and account a wearing event for each stethoscope.

In this regard, and returning to FIG. 1, the system 10 of this invention disclosure furthermore optionally includes an apparatus generally identified by reference numeral 60 for tracking or taking into account usage or a wearing event of each particular stethoscope 32. In a preferred embodiment, apparatus 60 includes a coral 62 for the stethoscopes 32. In one form, such coral 62 is attached to a suitable support S (FIG. 16) preferably situated at a location convenient to a plurality of the care givers/health care providers. In one form, and as shown in FIGS. 1 and 16, the coral 62 includes individualized depositories 62*a*, 62*b*, 62*c*, and etc. which are assigned to a particular health care provider/care giver and, accordingly, to the personalized or individualized stethoscope 32 associated with that particular care giver.

Figure 16:
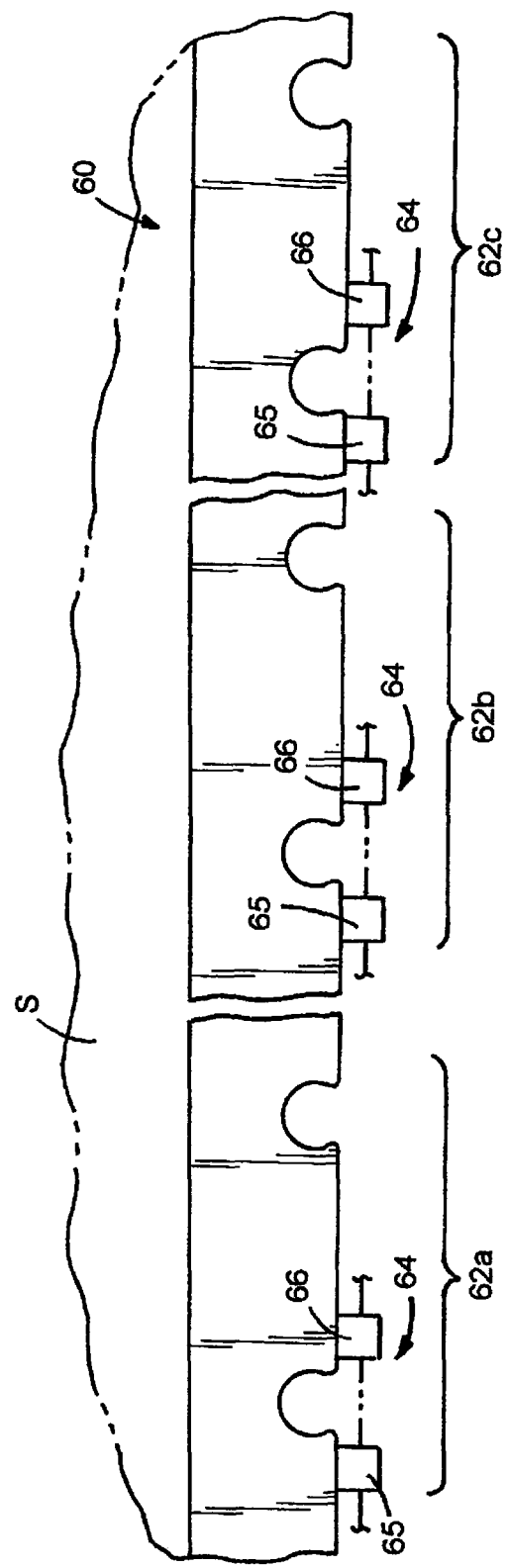
FIG. 16 is an enlarged schematic view of a coral shown in FIG. 1 for releasably holding one or more stethoscopes.

In the embodiment shown by way of example in FIG. 16, each depository 62*a*, 62*b*, 62*c*, and etc. is configured to releasably receive and hold a suitable portion of a particular stethoscope therewithin when such stethoscope is not in use. Preferably, the coral 62 further includes suitable sensor technology 64 associated with each depository 62*a*, 62*b* 62*c* and etc. In one form, such sensor technology 64 may be in the form of a conventional photoelectric sensor including one sensor element 65 for generating a light beam and another sensor element 66 for receiving the light beam. Sensor element 65 may be electrically powered through any suitable source of power. Of course, and as is conventional, when the light beam is broken or otherwise interrupted, indicative of the stethoscope 32 associated with that particular depository being removed therefrom, sensor element 66 delivers a signal to the analysis unit 20 of system 10. As such, a wearing event of each stethoscope 32 in the group of stethoscopes 34 (FIG. 1) can be tracked and recorded. It will be appreciated, any suitable sensor arrangement other the photoelectric sensors illustrated by way of example can be used for detecting when a particular stethoscope is removed and/or returned to the coral 62.

The analysis unit 20 and the plurality of sensors 64 operably associated with apparatus 60 and coral 62 preferably communicate through the conventional wired network described above, for example a local area network (LAN) and wide area network (WAN), or a wireless network, for example a wireless LAN (WLAN) and/or a wireless personal area network (WPAN). The wearing events (or lack thereof) measured for each particular stethoscope can then be evaluated by the analysis unit 20 against other work schedules and cleaning events to determine the cleaning efforts of that particular healthcare provider.

Figure 17:
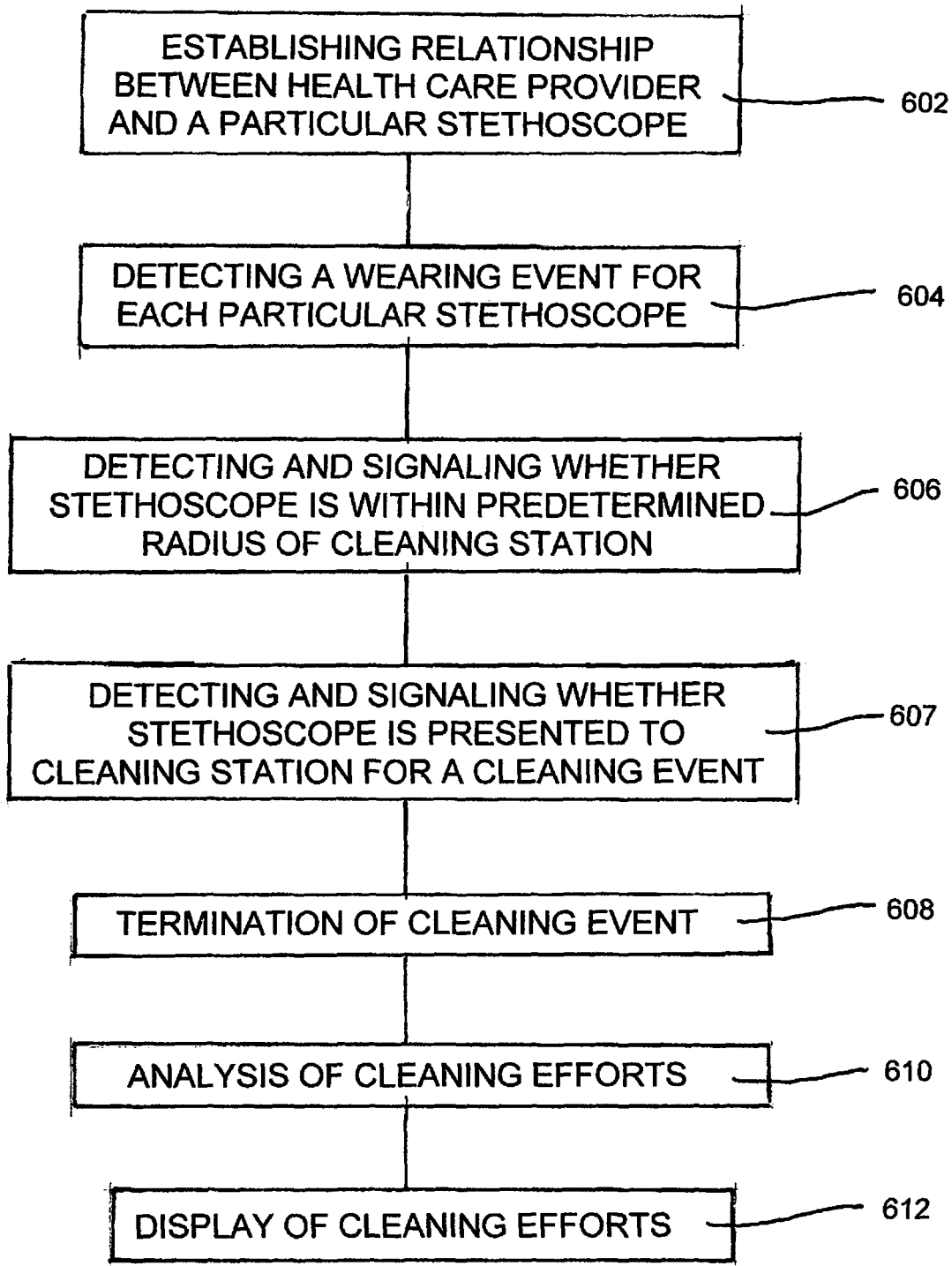
FIG. 17 is a flow chart of a method for monitoring cleaning efforts of care givers using stethoscopes according to some embodiments of this invention disclosure.

Turning now to FIG. 17, there is shown a flow chart of one method for monitoring cleaning efforts of persons using stethoscopes according to some embodiments of the present invention disclosure. Though the method described involves a process of monitoring cleaning efforts of a care giver using a particular stethoscope, it should be appreciated that the process involved can be implemented simultaneously by a plurality of individuals/care givers. Moreover, and while the method described involves a process of monitoring cleaning efforts for a conventional stethoscope through use of an apparatus involving those features and elements described above, it should be appreciated the cleaning event involved can use devices and technology different from that described above without seriously departing from the novel spirit and broad scope of this invention disclosure.

First, at Step 602, a relationship is established between a health care provider/care giver and a personal stethoscope in a group of stethoscopes. In the example shown in FIG. 1, the identification apparatus or device 30 operably associated with a personal or particular stethoscope 32 serves to identify each stethoscope 32 in the group 34 of conventional stethoscopes As such, and by being operably associated with a particular stethoscope, the identification apparatus or device 30 furthermore serves to identify the particular healthcare provider associated with that particular stethoscope. Optionally, the identification apparatus or device 30 on the particular stethoscope matches an ID associated with a user profile managed by the analysis unit 20 of system 10. As mentioned above, such identification apparatus or device 30 can be in the form of a tag or the like having a readable code imprinted or otherwise provided thereon or an RFID device which automatically identifies to a reader a particular stethoscope 32 in the group of stethoscopes 34.

At step 604, a wearing event of a particular stethoscope in the group of stethoscopes 36 is optimally monitored. That is, at Step 604 the removal of any stethoscope 32 from the coral or apparatus 60 (FIG. 1) is detected and/or read and a signal is delivered or otherwise transferred to the analysis unit 20 indicative of a wearing event for that particular stethoscope. Optionally, and when a particular stethoscope having an RFID device operably associated therewith passes a reader or the like, such action or wearing event associated with that particular stethoscope 32 is monitored and the signal delivered to the analysis unit 20 allows unit 20 to operably calculate the date and time when the particular stethoscope was being worn or otherwise used by the healthcare provider. Also at Step 604, the termination of such wearing event can be read or otherwise sensed and a signal delivered to unit 20 to allow unit 20 to operably calculate the date and time associated with the termination of such a wearing event.

As such, the analysis unit 20 optionally takes into account the time period or duration during which cleaning events for that particular stethoscope were to be recorded and the frequency of such cleaning events calculated. Preferably, unit 20 is configured to calculate the cleaning events to which a particular stethoscope was subjected during the working hours of the healthcare provider associated with the particular stethoscope and not during other time periods of non-use, i.e., vacation days, sick days and other time periods wherein the healthcare provider would not necessarily be required to use their particular stethoscope.

At Step 606, system 10 determines whether a stethoscope 32 having an identification apparatus operably associated therewith has come within predetermined radius of a cleaning station 50. That is, when a particular stethoscope comes within a predetermined radius of a cleaning station 50 (FIG. 1), the identification apparatus 30 (FIG. 1), in whatever form, operably associated with the particular stethoscope reads or is otherwise sensed by mechanism or apparatus 40, in whatever form, and a signal is transferred or otherwise delivered to the analysis unit 20. That signal from mechanism 40 is received and used by the analysis unit 20 to record the exposure of that particular stethoscope coming within predetermined radius of the cleaning station to a possible need for a cleaning event to be preformed thereon. Optionally, at Step 606, the code on the particular stethoscope is read or otherwise sensed by the detection mechanism or apparatus 40, in whatever form, and the signal delivered to the analysis unit 20 whereby permitting the analysis unit 20 to operably calculate the date and time when the particular stethoscope was exposed thus raising the possible need to have a cleaning event performed thereon.

At Step 607, system 10 determines whether a stethoscope 32 having an identification apparatus operably associated and that has come within predetermined radius of a cleaning station 50 has been presented for a cleaning event at a cleaning station. That is, when a particular stethoscope is presented to a cleaning station 50 for a cleaning event, the identification apparatus 30, in whatever form, operably associated with the particular stethoscope is read or otherwise sensed by the mechanism or apparatus 40, in whatever form, and a signal is transferred or otherwise delivered to the analysis unit 20. That signal from mechanism 40 is received and used by the analysis unit 20 to record when that particular stethoscope coming within predetermined radius of the cleaning station is presented to the cleaning station for a cleaning event. Optionally, at Step 607, the code on the particular stethoscope is read or otherwise sensed by the detection or apparatus 40B and a signal is delivered to the analysis unit 20 whereby permitting the analysis unit 20 to operably calculate the date and time when the particular stethoscope was presented to have a cleaning event performed thereon.

At Step 608, and following a cleaning event being performed thereon, the particular stethoscope 32 is withdrawn or retracted from the cleaning and sanitizing unit 50. At Step 608, the retraction or removal of the stethoscope relative to the cleaning unit 50 is detected by the code on the particular stethoscope being read or otherwise sensed by apparatus 40B and a signal is transferred to the analysis unit 20. Optionally, and when a particular stethoscope is retracted or otherwise withdrawn relative to the cleaning station 50 a signal is delivered from apparatus 40B to the analysis 20 to indicate the termination of the cleaning event.

At Step 610, the analysis unit 20 operably calculates the cleaning efforts of each health care provider/care giver relative to each particular stethoscope 32 in the group of stethoscopes 36. That is, the analysis unit 20 calculates the cleaning efforts of each health care provider/care giver relative to each particular stethoscope 32 in the group of stethoscopes 36 using the information inputted thereto from the plurality of mechanisms and devices forming part of system 20. Optionally, and to accurately test the compliance of the care giver's cleaning efforts with given standards while also testing the quality of the cleaning events, the analysis unit 20 takes into account the recorded date and duration of the cleaning event as well as the frequency of the cleaning events. As mentioned, cleaning events which are missing from certain episodes are calculated by unit 20 and can be compared against the work schedule of the particular care giver. Optionally, unit 20 is configured to calculate performance levels of each care giver so as to reflect the care giver's attention to stethoscope cleanliness habits. Optionally, such performance levels can be compared by unit 20 against a given standard whereby yielding a compliance comparison with such standard. For example, a predetermined pattern of how many visits may occur for a given doctor's office may be compared to the number of cleaning events actually occurring at such an office whereby determining the care giver's attention to stethoscope cleanliness habits at such office. The scoring bases for and the results calculated by the analysis unit 20 can be optionally stored in the repository 25 of unit 20

At Step 612, the computed and comparative results developed by the analysis unit 20 can be selectively printed and displayed. Alternatively, and at Step 612, a report may be sent or otherwise generated and/or delivered to a particular care giver and/or others indicating the cleaning efforts being made regarding each of the stethoscopes in the group of stethoscopes.

Figure 18:
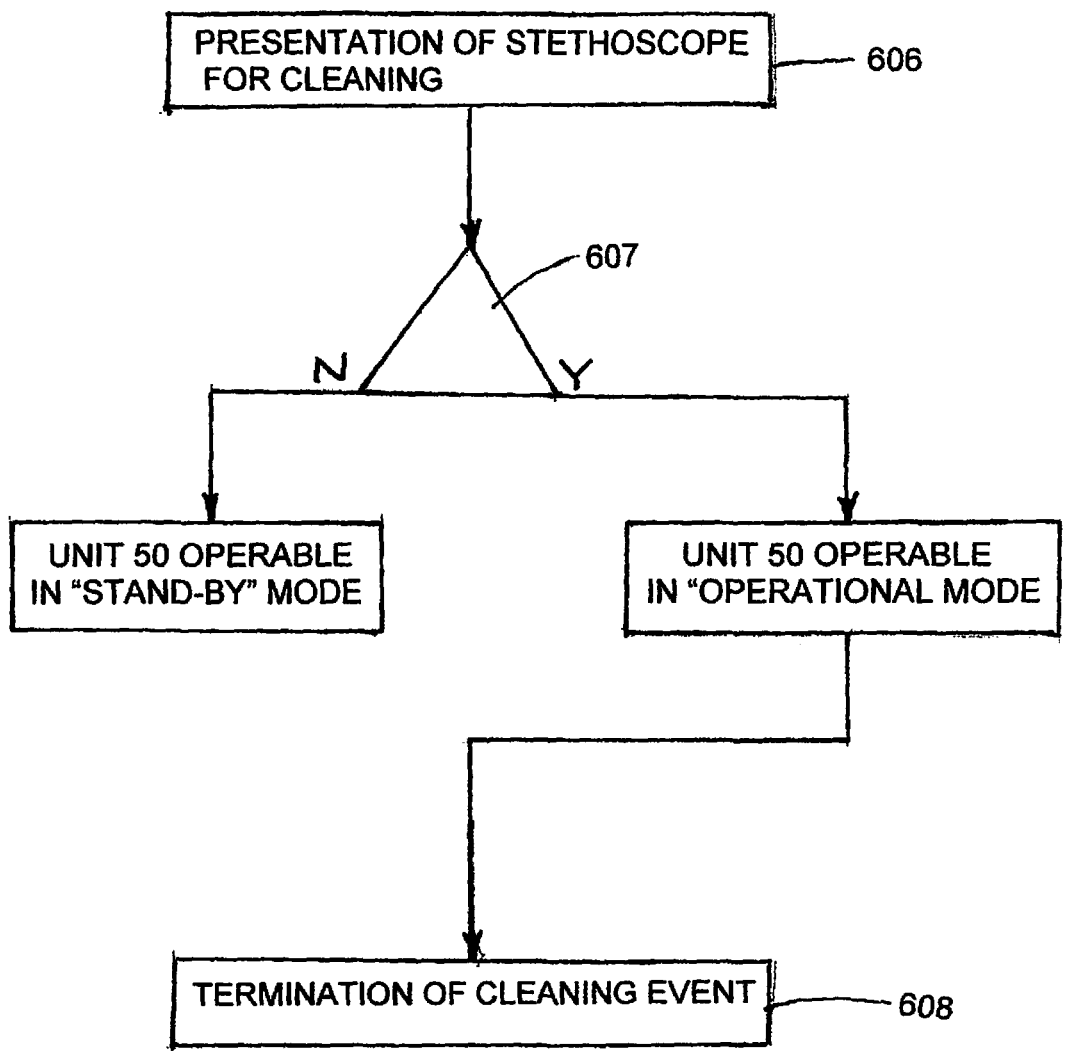
FIG. 18 schematically illustrates other optional Steps which may be utilized method for monitoring cleaning efforts of care givers using stethoscopes according to some embodiments of this invention disclosure.

When the identification apparatus 30, in whatever form, operably associated with any particular stethoscope is read or otherwise sensed by far field antenna 40A of the detection mechanism or apparatus 40, operation of the cleaning unit 50 is preferably enabled. As schematically illustrated in FIG. 18, at Step 606, and when the far field antenna 40A senses the identification apparatus 30 on any particular stethoscope so equipped comes within a predetermined radius thereof, the far field antenna 40A delivers a signal which causes the cleaning station 50 to operate in an "operational" mode whereby allowing a cleaning event to be affected on the head portion of the stethoscope presented to unit 50. On the other hand, at Step 606, when the far field antenna 40A senses the absence of an identification apparatus 30 on a stethoscope to be outside or beyond a predetermined range of operation, the cleaning unit 50 is switched to a "stand-by" mode.

From the foregoing, it will be observed that numerous modifications and variations can be made and effected without departing or detracting from the true spirit and novel concept of this invention disclosure. Moreover, it will be appreciated, the present disclosure is intended to set forth exemplifications which are not intended to limit the disclosure to the specific embodiments illustrated. Rather, this disclosure is intended to cover by the appended claims all such modifications and variations as fall within the spirit and scope of the claims.

What is claimed is:

1. A system for monitoring cleaning efforts of care givers using stethoscopes, said system comprising:
   one or more cleaning stations, with each station including a housing and cleaning apparatus disposed within said housing, with said cleaning apparatus being structured to clean a head portion of a stethoscope presented thereto;
   an identification apparatus operably associated with each of a plurality of stethoscopes for identifying each particular stethoscope;
   a first apparatus carried by the housing of each cleaning station and configured to detect, develop and send a first signal each time the identification apparatus operably associated with a particular stethoscope is disposed within a predetermined radius of a respective cleaning station;
   a second apparatus carried by the housing of each cleaning station and configured to detect, develop and send a second signal each time the identification apparatus operably associated with a particular stethoscope is presented to a cleaning apparatus of one of said cleaning stations to effect a cleaning event;
   a networked database system integrated with each cleaning station, with said database system including an analysis unit operably responsive to the first and second signals received from the first apparatus and the second apparatus, respectively, with said analysis unit being configured to calculate and develop information data indicative of the cleanliness level of each particular stethoscope having the identification apparatus operably associated therewith.

2. The system for monitoring cleaning efforts of care givers using stethoscopes according to claim 1, wherein each cleaning event is recorded only after the second apparatus detects the presence of the cleaning head of a particular stethoscope within a specified range of one of said cleaning stations for a predetermined time period.

3. The system for monitoring cleaning efforts of care givers using stethoscopes according to claim 1, further including a repository configured to store information received from said analysis unit regarding the presence of a particular stethoscope being detected by either said first apparatus and/or said second apparatus.

4. The system for monitoring cleaning efforts of care givers using stethoscopes according to claim 1, wherein with said database system further includes a monitoring apparatus operably connected to said analysis unit for taking into account actual usage of any one of said stethoscopes having said identification apparatus operably associated therewith and configured to develop data indicative of a wearing event for said stethoscope, with the cleanliness level of said stethoscope being at least partially determined by the data generated by said monitoring apparatus.

5. A system for monitoring cleaning efforts of care givers using stethoscopes, said system comprising:
   a plurality of cleaning stations disposed at different locations throughout a facility, with each cleaning station including a housing and a cleaning apparatus disposed within said housing, with said cleaning apparatus being structured to clean a head portion of a stethoscope presented thereto;
   an identification apparatus operative to identify an individual stethoscope in a group of stethoscopes;
   a fax field antenna carried by the housing of each cleaning station, with said far field antenna being designed and configured to detect, develop and send a first signal each time the identification apparatus associated with a particular stethoscope is disposed within a predetermined radius of a cleaning station;
   a near field antenna carried by the housing of each cleaning station, with said near field antenna being designed and configured to detect, develop and send a second signal each time the identification apparatus operably associated with a particular stethoscope is presented to a cleaning apparatus of one of cleaning stations to effect a cleaning event; and
   an analysis unit configured to compute data and the first and second signals from the near field and far field antennas of each cleaning station and calculate a duration of each cleaning event that has happened to an identified stethoscope at any of said cleaning stations so as to determine the cleanliness level of each stethoscope having the identification apparatus attached thereto partly as a function of the number of cleaning events for each identified stethoscope at one or more of said cleaning stations compared against a fixed value.

6. The system for monitoring cleaning efforts of care givers using stethoscopes according to claim 5, wherein each cleaning event is recorded after the said near field antenna senses the presence of the cleaning head of a particular stethoscope relative to one of the cleaning stations for a predetermined time period.

7. The system for monitoring cleaning efforts of care givers using stethoscopes according to claim 5, further including a repository configured to store information received from said analysis unit regarding the presence of a particular stethoscope being detected by either said far field antenna or said near field antenna.

8. The system for monitoring cleaning efforts of care givers using stethoscopes according to claim 7, wherein said repository is configured to store information regarding each time a particular stethoscope is presented within the predetermined radius of one of said cleaning stations.

9. The system for monitoring cleaning efforts of care givers using stethoscopes according to claim 5, further including an apparatus operably connected to said analysis unit and operative to monitor a wearing event for each stethoscope, and wherein the cleaning efforts for a particular stethoscope are partially evaluated as a function of the number of wearing events detected by said apparatus for monitoring wearing events.

10. The system for monitoring cleaning efforts of care givers using stethoscopes according to claim 5, further including an apparatus operably connected to said analysis unit for displaying an indication of the cleanliness of a particular stethoscope.

11. The system for monitoring cleaning efforts of care givers using stethoscopes according to claim 5, wherein said identification apparatus operably associated with each stethoscope in said group of stethoscopes includes an RFID device.

12. A system for monitoring cleaning efforts of care givers using stethoscopes, said system comprising:
- one or more cleaning stations, with each station including a cleaning apparatus structured to clean a head portion of a stethoscope presented thereto;
- an identification apparatus operably associated with each of a plurality of stethoscopes for identifying each particular stethoscope;
- a far field antenna carried by the housing of each cleaning station, with said far field antenna being designed and configured to detect, develop and send a first signal each time the identification apparatus associated with a particular stethoscope is disposed within a predetermined radius of a cleaning station;
- a near field antenna carried by the housing of each cleaning station, with said near field antenna being designed and configured to detect, develop and send a second signal each time the identification apparatus operably associated with a particular stethoscope is presented to a cleaning apparatus within one of said cleaning stations to effect a cleaning event; and
- an apparatus configured to generate a third signal indicative of whether said particular stethoscope having said identification apparatus operably associated therewith is timely presented to an adjacent cleaning station for a cleaning event, and wherein said timely presentation of said particular stethoscope to be cleaned requires said particular stethoscope to be presented to said cleaning station within a predetermined period of time following said near field antenna detecting when a particular stethoscope having an identification apparatus operably associated therewith comes within a specified radius of a cleaning station; and
- a networked analysis unit configured to compute data and the first and second signals from the near field and far field antennas, respectively, of each cleaning station and configured for calculating and developing information data representative of the cleanliness level of each particular stethoscope having the identification apparatus operably associated therewith.

13. The system for monitoring cleaning efforts of care givers using stethoscopes according to claim 12, wherein each cleaning event is recorded after the said near field antenna senses the presence of the cleaning head of a particular stethoscope relative to one of the cleaning stations for a predetermined time period.

14. The system for monitoring cleaning efforts of care givers using stethoscopes according to claim 12, further including a repository configured to store information data received from said analysis unit regarding the presence of a particular stethoscope being detected by either said far field antenna or said near field antenna.

15. The system for monitoring cleaning efforts of care givers using stethoscopes according to claim 14, wherein said repository is configured to store information data regarding each time a particular stethoscope is presented within the predetermined radius of one of said cleaning stations.

16. The system for monitoring cleaning efforts of care givers using stethoscopes according to claim 12, further including an apparatus operably connected to said analysis unit and operative to monitor a wearing event for each stethoscope, and wherein the cleaning efforts for a particular stethoscope are partially evaluated as a function of the number of wearing events detected by said apparatus for monitoring wearing events.

17. The system for monitoring cleaning efforts of care givers using stethoscopes according to claim 12, further including an apparatus operably connected to said analysis unit for displaying an indication of the cleanliness of a particular stethoscope.

18. A method for monitoring cleaning efforts of care givers using stethoscopes, said method comprising the steps of:
- establishing a relationship between a care giver and a particular stethoscope;
- providing a one or more cleaning stations, with each cleaning station including a housing and a cleaning apparatus disposed within the housing, with said cleaning apparatus being capable of cleaning a head portion of a stethoscope presented thereto for cleaning;
- providing a first apparatus carried on the housing of each cleaning apparatus and configured to detect and develop a first signal when a particular stethoscope comes within a predetermined radius of said cleaning station;
- providing a second apparatus carried on the housing of each cleaning apparatus and configured to detect and develop a second signal when a particular stethoscope is presented to said cleaning station for a cleaning event; and
- computing data including the first and second signals from said first and second apparatus, respectively, of each cleaning station to calculate and develop informational data representative of the cleanliness level of each stethoscope having an established relationship with a care giver.

19. The method for monitoring cleaning efforts of care givers using stethoscopes according to claim 18, with said method comprising the further step of:
- recording when each particular stethoscope is presented to said cleaning station for a cleaning event only after each particular stethoscope is presented to said cleaning station for a predetermined period of time.

20. The method for monitoring cleaning efforts of care givers using stethoscopes according to claim 18, wherein said method comprises the further step of:
- storing in a networked repository each time a particular stethoscope is presented to said cleaning station for a cleaning event.

21. The method for monitoring cleaning efforts of care givers using stethoscopes according to claim 18, wherein said method comprises the further step of:
- monitoring wearing events for each stethoscope, and wherein each cleaning effort is partly evaluated according to the number of monitored wearing events.

22. The method for monitoring cleaning efforts of care givers using stethoscopes according to claim 18, and wherein each cleaning station includes an enclosure defining a port through which the head portion of the stethoscope moves to effect the cleaning event.

23. The method for monitoring cleaning efforts of care givers using stethoscopes according to claim 18, wherein said method comprises the further step of:
- comparing the number of cleaning events for a particular stethoscope against a predetermined value to determine the cleanliness level of said particular stethoscope.

* * * * *